(12) United States Patent
Luftig

(10) Patent No.: US 6,328,976 B1
(45) Date of Patent: Dec. 11, 2001

(54) NON-INFECTIOUS, PROTEASE DEFECTIVE HIV PARTICLES AND NUCLEIC ACID MOLECULES ENCODING THEREFOR

(75) Inventor: Ronald B. Luftig, Metairie, LA (US)

(73) Assignee: Immune Response Corporation, Carlsbad, CA (US)

( * ) Notice: Subject to any disclaimer, the term of this patent is extended or adjusted under 35 U.S.C. 154(b) by 0 days.

(21) Appl. No.: 09/055,075

(22) Filed: Apr. 3, 1998

Related U.S. Application Data
(60) Provisional application No. 60/043,047, filed on Apr. 4, 1997.

(51) Int. Cl.[7] ............................ A61K 39/21; A61K 38/00; A61K 38/04
(52) U.S. Cl. .................. 424/208.1; 530/324; 530/329
(58) Field of Search ........................ 424/208.1; 530/324, 530/329

(56) References Cited

PUBLICATIONS

Bahmani et al., "Production of doughnut–shaped, protease–defective particles from a human T cell clone carrying a provirus with specific mutations in the env, pol, vpr, and nef genes," *AIDS Research and Human Retroviruses* 13:523–526 (1997).

Ikuta et al., "AIDS pathogenesis: the role of accessory gene mutations, leading to formation of long–lived persistently infected cells and/or apoptotsis–inducing HIV–1 particles," *Virus Research* 52:145–156 (1997).

Kameoka et al., "Induction of apoptosis by protease–defective particle preparations of human immunodeficiency virus type 1 is specific to a subset of U937–derived subclones," *International Immunology* 8:1687–1697 (1996).

Kameoka et al., "Exposure of resting peripheral blood T cells to HIV–1 particles generates CD25+ killer cells in a small subset, leading to induction of apoptosis in bystander cells," *International Immunology* 9:1453–1462 (1997).

Kameoka et al., "Protease–defective, gp120–containing human immunodeficiency virus type 1 particles induce apoptosis more efficiently than does wild–type virus or recombinant gp 120 protein in healthy donor–derived peripheral blood T cells," *J. Clin. Microbiology* 35:41–47 (1997).

Kishi et al., "Naturally occurring accessory gene mutations lead to persistent human immunodeficiency virus type 1 infection of CD4–positive T cells," *J. Virology* 69:7507–7518 (1995).

Luftig and Ikuta, "Are defective, HIV protease–deficient particles the real culprit in AIDS," *ASM News* 60:417–419 (1994).

Nakano et al., "Analysis of POL gene of a non–infectious HIV–1 clone," *Abstract* 1:PA0043 (1994).

Ohki et al., "Noninfectious doughnut–shaped human immunodeficiency virus type 1 can induce syncytia mediated by fusion of the particles with CD4–positive cells," *J. Acquired Immune Deficiency Syndromes* 4:1233–1240 (1991).

Otake et al., "The carboxyl–terminal region of HIV–1 nef protein is a cell surface domain that can interact with CD4+ T cells," *J. Immunol.* 153:5826–5837 (1994).

Wang et al., "Particle assembly and Vpr expression in human immunodeficiency virus type 1–infected cells demostrated by immunoelectron microscopy," *J. General Virology* 75:2607–2614 (1994).

Yunoki et al., "Production of infectious particles from defective human immunodeficiency virus type 1 (HIV–1)–producing cell clones by superinfection with infectious HIV–1," *Arch. Virol.* 116:143–158 (1991).

*Primary Examiner*—Hankyel T. Park
(74) *Attorney, Agent, or Firm*—Campbell & Flores LLP

(57) ABSTRACT

This invention is directed toward mutated DNA, proteins, or protein fragments and particles from the L-2 cell line. The invention is also directed to diagnostic, prophylactic and therapeutic methods of making and using the DNA, proteins and particles.

22 Claims, 5 Drawing Sheets

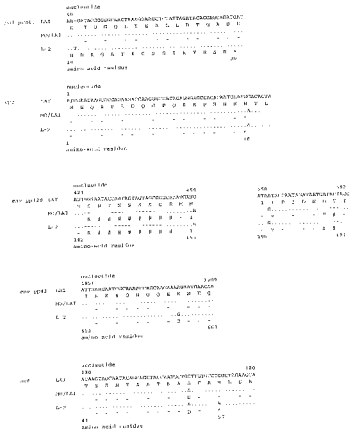

```
pol prot.  LAI   nucleotide
                 40
                 AA-GATAGGGGGCAACTAAAGGAAGCTCTATTAGATACAGGAGCAGATGAT
                  K  I  G  G  Q  L  K  E  A  L  L  D  T  G  A  D  D
           MO/LAI ..................................................
                  -  -  -  -  -  -  -  -  -  -  -  -  -  -  -  -  -
           L-2    ..T...............................................
                  N  D  R  G  A  T  K  G  S  S  I  R  Y  R  S  R  *
                  14                                              30
                 amino-acid residue vpr        LAI   nucleotide
                 1
                 ATGGAACAAGCCCCAGAAGACCAAGGCCACAGAGGAGCCACACAATGAATGGACACTA
                  M  E  Q  A  P  E  D  Q  G  P  Q  R  E  P  H  N  E  W  T  L
           MO/LAI .........................................................A......
                  -  -  -  -  -  -  -  -  -  -  -  -  -  -  -  -  -  *
           L-2    .........................................................A......
                  -  -  -  -  -  -  -  -  -  -  -  -  -  -  -  -  -  *
                  1                                                       18
                 amino-acid residue
```

FIG. 1A

```
                    nucleotide
                    424                                         459
env gp120   LAI     AGTAGTAATACCAATAGTAGTAGCGGGGAAATGATG
                     S  S  N  T  N  S  S  S  G  E  M  M
            MO/LAI  ...............................A
                     -  #  -  -  -  -  -  #  -  -  -  I
            L-2     ...............................A
                     -  R  #  #  #  #  #  #  #  -  -  I
                    142                                         153
                    amino-acid residue 558                                         582
                    ATAATACCAATAGATAATGATACTACC
                     I  I  P  I  D  N  D  T  T
                    ...G.......................
                     -  -  V  -  -  -  -  -  -
                    ...G.......................
                     -  -  V  -  -  -  -  -  -
                    186                               194
```

FIG. 1B

```
env gp41   LAI     nucleotide
                   1951                                              1989
                   ATTGAAGAATCGCAAAACCAGCAAGAAAAGAATGAACAA
                    I   E   E   S   Q   N   Q   Q   E   K   N   E   Q
           MO/LAI  ......................................
                    -   -   -   -   -   -   -   -   -   -   -   -   -
           L-2     ..................G...................
                    -   -   -   -   -   -   -   -   R   -   -   -   -
                   651                                              663
                   amino-acid residue nef        LAI     nucleotide
                   130                                               180
                   ACAAGTAGCAATACAGCAGCTACCAATGCTGCTTGTGCCTGGCTAGAAGCA
                    T   S   S   N   T   A   A   T   N   A   A   C   A   W   L   E   A
           MO/LAI  .........................A..........D.............
                    -   -   -   -   -   -   -   -   -   -   -   -   -   -   -   -   -
           L-2     .................................A........A......
                    -   -   -   -   -   -   -   -   -   -   -   -   D   -   -   *   -
                   44                                                57
                   amino acid residue
```

FIG. 1C

PRIMERS USED FOR PCR AMPLIFICATION OF HIV-1 PROVIRUS IN L-2

| Primer | | Nucleotide No. | Sequence | Target gene(s) | Amplified size (bp) |
|---|---|---|---|---|---|
| gag-d | Sense | (1921-1942) | 5' CAGAAAGGCAATTTTTAGGAACC 3' | pol (protease) | 670 |
| JA-20 | Antisense | (2590-2571) | 5' CCTGGCTTTAATTTTACTGG 3' | | |
| pol-3 | Sense | (4808-4826) | 5' GTACAGGGGAAAGAATA 3' | vif, vpr, vpu | 1538 |
| env-3 | Antisense | (6341-6317) | 5' CCCCATAATAGACTGTGACCCACAA 3' | | |
| EN-D-Sal | Sense | (6221-6238) | 5' TGAGTCGACATGAGAGTGAAGGAGAAATAT 3' | env (gp120, gp41) | 2562 |
| EA-Pst | Antisense | (8782-8763) | 5' TCCTGCAGCTTATAGCAAAATCCTTTCCA 3' | | |
| EN53 | Sense | (8655-8678) | 5' TCAATGCCACAGCCATAGCCAGTAG 3' | nef | 934 |
| LR3 | Antisense | (9588-9568) | 5' CAGTGGGTTCCCTAGTTAGCC 3' | | |

FIG. 2

```
1                    11                   21                   31                   41
ATGGGTGGCA           AGTGGTCAAA           AAGTAGTGTG           GTTGGATGGC           CT(G)CTGTAAG 51                   61                   71                   81                   91
GGAAA(A)AATG         AGCGAGCTG            AGACAGCAGC           AGATGGGGTG           GGAGCAG(T)AT 101                  111                  121                  131                  141
CTCGAGACCT           (A)GAAAAA CAT        GGAGCAATCA           CAAGTAGCAA           TACAGCAGCT 151                  161                  171
ACCAATGCTG           (A)TTGTGCCT(A)       GCTAGAAGCA 181                  201
CAAGAGGAGG           TT - - - -
AGGAGGTGGG
```

FIG. 3

(amino) - NH$_2$ - MGGKWSKSSV VGWP(A)VRE(K)MRRAEPAADGV GA(V)SRDLEKH GAIT
SSNTAA TNA(D)CA - COOH (carboxy)

FIG. 4

SEQUENCE LISTING

<160> NUMBER OF SEQ ID NOS: 48

<210> SEQ ID NO 1
<211> LENGTH: 51
<212> TYPE: DNA
<213> ORGANISM: Human immunodeficiency virus type 1
<220> FEATURE:
<221> NAME/KEY: CDS
<222> LOCATION: (1)..(51)

<400> SEQUENCE: 1

```
aag ata ggg ggg caa cta aag gaa gct cta tta gat aca gga gca gat      48
Lys Ile Gly Gly Gln Leu Lys Glu Ala Leu Leu Asp Thr Gly Ala Asp
  1               5                  10                  15 gat                                                                  51
Asp
```

<210> SEQ ID NO 2
<211> LENGTH: 17
<212> TYPE: PRT
<213> ORGANISM: Human immunodeficiency virus type 1

<400> SEQUENCE: 2

```
Lys Ile Gly Gly Gln Leu Lys Glu Ala Leu Leu Asp Thr Gly Ala Asp
  1               5                  10                  15

Asp
```

<210> SEQ ID NO 3
<211> LENGTH: 51
<212> TYPE: DNA
<213> ORGANISM: Human immunodeficiency virus type 1
<220> FEATURE:
<221> NAME/KEY: CDS
<222> LOCATION: (1)..(51)

<400> SEQUENCE: 3

```
aag ata ggg ggg caa cta aag gaa gct cta tta gat aca gga gca gat      48
Lys Ile Gly Gly Gln Leu Lys Glu Ala Leu Leu Asp Thr Gly Ala Asp
  1               5                  10                  15 gat                                                                  51
Asp
```

<210> SEQ ID NO 4
<211> LENGTH: 17
<212> TYPE: PRT
<213> ORGANISM: Human immunodeficiency virus type 1

<400> SEQUENCE: 4

```
Lys Ile Gly Gly Gln Leu Lys Glu Ala Leu Leu Asp Thr Gly Ala Asp
  1               5                  10                  15

Asp
```

<210> SEQ ID NO 5
<211> LENGTH: 52
<212> TYPE: DNA
<213> ORGANISM: Human immunodeficiency virus type 1
<220> FEATURE:
<221> NAME/KEY: CDS
<222> LOCATION: (1)..(51)

<400> SEQUENCE: 5

```
aat gat agg ggg gca act aaa gga agc tct att aga tac agg agc aga      48
Asn Asp Arg Gly Ala Thr Lys Gly Ser Ser Ile Arg Tyr Arg Ser Arg
```

-continued

```
           1               5              10             15 tga t                                                             52

<210> SEQ ID NO 6
<211> LENGTH: 16
<212> TYPE: PRT
<213> ORGANISM: Human immunodeficiency virus type 1

<400> SEQUENCE: 6

Asn Asp Arg Gly Ala Thr Lys Gly Ser Ser Ile Arg Tyr Arg Ser Arg
  1               5                  10                  15

<210> SEQ ID NO 7
<211> LENGTH: 60
<212> TYPE: DNA
<213> ORGANISM: Human immunodeficiency virus type 1
<220> FEATURE:
<221> NAME/KEY: CDS
<222> LOCATION: (1)..(60)

<400> SEQUENCE: 7 atg gaa caa gcc cca gaa gac caa ggg cca cag agg gag cca cac aat    48
Met Glu Gln Ala Pro Glu Asp Gln Gly Pro Gln Arg Glu Pro His Asn
  1               5                  10                  15 gaa tgg aca cta                                                    60
Glu Trp Thr Leu
            20

<210> SEQ ID NO 8
<211> LENGTH: 20
<212> TYPE: PRT
<213> ORGANISM: Human immunodeficiency virus type 1

<400> SEQUENCE: 8

Met Glu Gln Ala Pro Glu Asp Gln Gly Pro Gln Arg Glu Pro His Asn
  1               5                  10                  15

Glu Trp Thr Leu
            20

<210> SEQ ID NO 9
<211> LENGTH: 60
<212> TYPE: DNA
<213> ORGANISM: Human immunodeficiency virus type 1
<220> FEATURE:
<221> NAME/KEY: CDS
<222> LOCATION: (1)..(54)

<400> SEQUENCE: 9 atg gaa caa gcc cca gaa gac caa ggg cca cag agg gag cca cac aat    48
Met Glu Gln Ala Pro Glu Asp Gln Gly Pro Gln Arg Glu Pro His Asn
  1               5                  10                  15 gaa tga acacta                                                     60
Glu

<210> SEQ ID NO 10
<211> LENGTH: 17
<212> TYPE: PRT
<213> ORGANISM: Human immunodeficiency virus type 1

<400> SEQUENCE: 10

Met Glu Gln Ala Pro Glu Asp Gln Gly Pro Gln Arg Glu Pro His Asn
  1               5                  10                  15

Glu
```

```
<210> SEQ ID NO 11
<211> LENGTH: 60
<212> TYPE: DNA
<213> ORGANISM: Human immunodeficiency virus type 1
<220> FEATURE:
<221> NAME/KEY: CDS
<222> LOCATION: (1)..(54)

<400> SEQUENCE: 11 atg gaa caa gcc cca gaa gac caa ggg cca cag agg gag cca cac aat        48
Met Glu Gln Ala Pro Glu Asp Gln Gly Pro Gln Arg Glu Pro His Asn
 1               5                  10                  15 gaa tga acacta                                                         60
Glu

<210> SEQ ID NO 12
<211> LENGTH: 17
<212> TYPE: PRT
<213> ORGANISM: Human immunodeficiency virus type 1

<400> SEQUENCE: 12

Met Glu Gln Ala Pro Glu Asp Gln Gly Pro Gln Arg Glu Pro His Asn
 1               5                  10                  15
Glu

<210> SEQ ID NO 13
<211> LENGTH: 36
<212> TYPE: DNA
<213> ORGANISM: Human immunodeficiency virus type 1
<220> FEATURE:
<221> NAME/KEY: CDS
<222> LOCATION: (1)..(36)

<400> SEQUENCE: 13 agt agt aat acc aat agt agt agc ggg gaa atg atg                        36
Ser Ser Asn Thr Asn Ser Ser Ser Gly Glu Met Met
 1               5                  10

<210> SEQ ID NO 14
<211> LENGTH: 12
<212> TYPE: PRT
<213> ORGANISM: Human immunodeficiency virus type 1

<400> SEQUENCE: 14

Ser Ser Asn Thr Asn Ser Ser Ser Gly Glu Met Met
 1               5                  10

<210> SEQ ID NO 15
<211> LENGTH: 12
<212> TYPE: DNA
<213> ORGANISM: Human immunodeficiency virus type 1
<220> FEATURE:
<221> NAME/KEY: misc_feature
<222> LOCATION: (4)..(6)
<223> OTHER INFORMATION: any nucleotides that code for Arg.

<400> SEQUENCE: 15
agtmgnatga ta                                                          12

<210> SEQ ID NO 16
<211> LENGTH: 4
<212> TYPE: PRT
<213> ORGANISM: Human immunodeficiency virus type 1

<400> SEQUENCE: 16
```

```
<210> SEQ ID NO 17
<211> LENGTH: 12
<212> TYPE: DNA
<213> ORGANISM: Human immunodeficiency virus type 1
<220> FEATURE:
<221> NAME/KEY: misc_feature
<222> LOCATION: (4)..(6)
<223> OTHER INFORMATION: any nucleotides coding for Arg

<400> SEQUENCE: 17
agtmgnatga ta                                                    12

<210> SEQ ID NO 18
<211> LENGTH: 4
<212> TYPE: PRT
<213> ORGANISM: Human immunodeficiency virus type 1

<400> SEQUENCE: 18

Ser Arg Met Ile
  1

<210> SEQ ID NO 19
<211> LENGTH: 27
<212> TYPE: DNA
<213> ORGANISM: Human immunodeficiency virus type 1
<220> FEATURE:
<221> NAME/KEY: CDS
<222> LOCATION: (1)..(27)

<400> SEQUENCE: 19 ata ata cca ata gat aat gat act acc                              27
Ile Ile Pro Ile Asp Asn Asp Thr Thr
  1               5

<210> SEQ ID NO 20
<211> LENGTH: 9
<212> TYPE: PRT
<213> ORGANISM: Human immunodeficiency virus type 1

<400> SEQUENCE: 20

Ile Ile Pro Ile Asp Asn Asp Thr Thr
  1               5

<210> SEQ ID NO 21
<211> LENGTH: 21
<212> TYPE: DNA
<213> ORGANISM: Human immunodeficiency virus type 1
<220> FEATURE:
<221> NAME/KEY: CDS
<222> LOCATION: (1)..(21)

<400> SEQUENCE: 21 ata gta cca ata gat aat acc                                      21
Ile Val Pro Ile Asp Asn Thr
  1               5

<210> SEQ ID NO 22
<211> LENGTH: 7
<212> TYPE: PRT
<213> ORGANISM: Human immunodeficiency virus type 1

<400> SEQUENCE: 22

Ile Val Pro Ile Asp Asn Thr
  1               5
```

```
<210> SEQ ID NO 23
<211> LENGTH: 21
<212> TYPE: DNA
<213> ORGANISM: Human immunodeficiency virus type 1
<220> FEATURE:
<221> NAME/KEY: CDS
<222> LOCATION: (1)..(21)

<400> SEQUENCE: 23 ata gta cca ata gat aat acc                                          21
Ile Val Pro Ile Asp Asn Thr
 1               5

<210> SEQ ID NO 24
<211> LENGTH: 7
<212> TYPE: PRT
<213> ORGANISM: Human immunodeficiency virus type 1

<400> SEQUENCE: 24

Ile Val Pro Ile Asp Asn Thr
 1               5

<210> SEQ ID NO 25
<211> LENGTH: 39
<212> TYPE: DNA
<213> ORGANISM: Human immunodeficiency virus type 1
<220> FEATURE:
<221> NAME/KEY: CDS
<222> LOCATION: (1)..(39)

<400> SEQUENCE: 25 att gaa gaa tcg caa aac cag caa gaa aag aat gaa caa                  39
Ile Glu Glu Ser Gln Asn Gln Gln Glu Lys Asn Glu Gln
 1               5                   10

<210> SEQ ID NO 26
<211> LENGTH: 13
<212> TYPE: PRT
<213> ORGANISM: Human immunodeficiency virus type 1

<400> SEQUENCE: 26

Ile Glu Glu Ser Gln Asn Gln Gln Glu Lys Asn Glu Gln
 1               5                   10

<210> SEQ ID NO 27
<211> LENGTH: 39
<212> TYPE: DNA
<213> ORGANISM: Human immunodeficiency virus type 1
<220> FEATURE:
<221> NAME/KEY: CDS
<222> LOCATION: (1)..(39)

<400> SEQUENCE: 27 att gaa gaa tcg caa aac cag caa gaa aag aat gaa caa                  39
Ile Glu Glu Ser Gln Asn Gln Gln Glu Lys Asn Glu Gln
 1               5                   10

<210> SEQ ID NO 28
<211> LENGTH: 13
<212> TYPE: PRT
<213> ORGANISM: Human immunodeficiency virus type 1

<400> SEQUENCE: 28

Ile Glu Glu Ser Gln Asn Gln Gln Glu Lys Asn Glu Gln
 1               5                   10
```

```
<210> SEQ ID NO 29
<211> LENGTH: 39
<212> TYPE: DNA
<213> ORGANISM: Human immunodeficiency virus type 1
<220> FEATURE:
<221> NAME/KEY: CDS
<222> LOCATION: (1)..(39)

<400> SEQUENCE: 29 att gaa gaa tcg caa aac cag caa gaa agg aat gaa caa        39
Ile Glu Glu Ser Gln Asn Gln Gln Glu Arg Asn Glu Gln
 1               5                  10

<210> SEQ ID NO 30
<211> LENGTH: 13
<212> TYPE: PRT
<213> ORGANISM: Human immunodeficiency virus type 1

<400> SEQUENCE: 30

Ile Glu Glu Ser Gln Asn Gln Gln Glu Arg Asn Glu Gln
 1               5                  10

<210> SEQ ID NO 31
<211> LENGTH: 51
<212> TYPE: DNA
<213> ORGANISM: Human immunodeficiency virus type 1
<220> FEATURE:
<221> NAME/KEY: CDS
<222> LOCATION: (1)..(51)

<400> SEQUENCE: 31 aca agt agc aat aca gca gct acc aat gct gct tgt gcc tgg cta gaa    48
Thr Ser Ser Asn Thr Ala Ala Thr Asn Ala Ala Cys Ala Trp Leu Glu
 1               5                  10                  15 gca                                                                51
Ala

<210> SEQ ID NO 32
<211> LENGTH: 17
<212> TYPE: PRT
<213> ORGANISM: Human immunodeficiency virus type 1

<400> SEQUENCE: 32

Thr Ser Ser Asn Thr Ala Ala Thr Asn Ala Ala Cys Ala Trp Leu Glu
 1               5                  10                  15

Ala

<210> SEQ ID NO 33
<211> LENGTH: 51
<212> TYPE: DNA
<213> ORGANISM: Human immunodeficiency virus type 1

<400> SEQUENCE: 33
acaagtagca atacagcagc taccaatgct gattgtgcct ggctagaagc a           51

<210> SEQ ID NO 34
<211> LENGTH: 17
<212> TYPE: PRT
<213> ORGANISM: Human immunodeficiency virus type 1

<400> SEQUENCE: 34

Thr Ser Ser Asn Thr Ala Ala Thr Asn Ala Ala Cys Ala Trp Leu Glu
 1               5                  10                  15

Ala
```

<210> SEQ ID NO 35
<211> LENGTH: 51
<212> TYPE: DNA
<213> ORGANISM: Human immunodeficiency virus type 1
<220> FEATURE:
<221> NAME/KEY: CDS
<222> LOCATION: (1)..(42)

<400> SEQUENCE: 35 aca agt agc aat aca gca gct acc aat gct gat tgt gcc tag ctagaagca    51
Thr Ser Ser Asn Thr Ala Ala Thr Asn Ala Asp Cys Ala
  1               5                  10

<210> SEQ ID NO 36
<211> LENGTH: 13
<212> TYPE: PRT
<213> ORGANISM: Human immunodeficiency virus type 1

<400> SEQUENCE: 36

Thr Ser Ser Asn Thr Ala Ala Thr Asn Ala Asp Cys Ala
  1               5                  10

<210> SEQ ID NO 37
<211> LENGTH: 22
<212> TYPE: DNA
<213> ORGANISM: Artificial Sequence
<220> FEATURE:
<223> OTHER INFORMATION: Description of Artificial Sequence: Synthetic
      Nucleotide

<400> SEQUENCE: 37
cagaaaggca attttaggaa cc                                              22

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence: Synthetic
      Nucleotide

<400> SEQUENCE: 38
cctggcttta attttactgg                                                 20

<210> SEQ ID NO 39
<211> LENGTH: 17
<212> TYPE: DNA
<213> ORGANISM: Artificial Sequence
<220> FEATURE:
<223> OTHER INFORMATION: Description of Artificial Sequence: Synthetic
      Nucleotide

<400> SEQUENCE: 39
gtacagggga aagaata                                                    17

<210> SEQ ID NO 40
<211> LENGTH: 25
<212> TYPE: DNA
<213> ORGANISM: Artificial Sequence
<220> FEATURE:
<223> OTHER INFORMATION: Description of Artificial Sequence: Synthetic
      Nucleotide

<400> SEQUENCE: 40
ccccataata gactgtgacc cacaa                                           25

-continued

<210> SEQ ID NO 41
<211> LENGTH: 30
<212> TYPE: DNA
<213> ORGANISM: Artificial Sequence
<220> FEATURE:
<223> OTHER INFORMATION: Description of Artificial Sequence: Synthetic
      Nucleotide

<400> SEQUENCE: 41
tgagtcgaca tgagagtgaa ggagaaatat                                          30

<210> SEQ ID NO 42
<211> LENGTH: 29
<212> TYPE: DNA
<213> ORGANISM: Artificial Sequence
<220> FEATURE:
<223> OTHER INFORMATION: Description of Artificial Sequence: Synthetic
      Nucleotide

<400> SEQUENCE: 42
tcctgcagct tatagcaaaa tcctttcca                                           29

<210> SEQ ID NO 43
<211> LENGTH: 24
<212> TYPE: DNA
<213> ORGANISM: Artificial Sequence
<220> FEATURE:
<223> OTHER INFORMATION: Description of Artificial Sequence: Synthetic
      Nucleotide

<400> SEQUENCE: 43
tcaatgccac agccatagca gtag                                                24

<210> SEQ ID NO 44
<211> LENGTH: 21
<212> TYPE: DNA
<213> ORGANISM: Artificial Sequence
<220> FEATURE:
<223> OTHER INFORMATION: Description of Artificial Sequence: Synthetic
      Nucleotide

<400> SEQUENCE: 44
cagtgggttc cctagttagc c                                                   21

<210> SEQ ID NO 45
<211> LENGTH: 202
<212> TYPE: DNA
<213> ORGANISM: Human immunodeficiency virus type 1

<400> SEQUENCE: 45
atgggtggca agtggtcaaa agtagtgtg gttggatggc ctgctgtaag ggaaaaaatg          60
agacgagctg agccagcagc agatggggtg ggagcagtat ctcgagacct agaaaaacat       120
ggagcaatca caagtagcaa tacagcagct accaatgctg attgtgccta gctagaagca       180
caagaggagg aggaggtggg tt                                                202

<210> SEQ ID NO 46
<211> LENGTH: 56
<212> TYPE: PRT
<213> ORGANISM: Human immunodeficiency virus type 1

<400> SEQUENCE: 46

Met Gly Gly Lys Trp Ser Lys Ser Ser Val Val Gly Trp Pro Ala Val
 1               5                  10                  15

-continued

```
Arg Glu Lys Met Arg Arg Ala Glu Pro Ala Ala Asp Gly Val Gly Ala
            20                  25                  30

Val Ser Arg Asp Leu Glu Lys His Gly Ala Ile Thr Ser Ser Asn Thr
        35                  40                  45

Ala Ala Thr Asn Ala Asp Cys Ala
     50                  55

<210> SEQ ID NO 47
<211> LENGTH: 202
<212> TYPE: DNA
<213> ORGANISM: Human immunodeficiency virus type 1

<400> SEQUENCE: 47
atgggtggca agtggtcaaa aagtagtgtg gttggatggc ctactgtaag ggaaagaatg      60
agacgagctg agccagcagc agatggggtg ggagcagcat ctcgagacct ggaaaaacat     120
ggagcaatca caagtagcaa tacagcagct accaatgctg cttgtgcctg gctagaagca     180
caagaggagg aggaggtggg tt                                              202

<210> SEQ ID NO 48
<211> LENGTH: 56
<212> TYPE: PRT
<213> ORGANISM: Human immunodeficiency virus type 1

<400> SEQUENCE: 48

Met Gly Gly Lys Trp Ser Lys Ser Ser Val Val Gly Trp Pro Thr Val
  1               5                  10                  15

Arg Glu Arg Met Arg Arg Ala Glu Pro Ala Ala Asp Gly Val Gly Ala
            20                  25                  30

Ala Ser Arg Asp Leu Glu Lys His Gly Ala Ile Thr Ser Ser Asn Thr
        35                  40                  45

Ala Ala Thr Asn Ala Ala Cys Ala
     50                  55
```

NON-INFECTIOUS, PROTEASE DEFECTIVE HIV PARTICLES AND NUCLEIC ACID MOLECULES ENCODING THEREFOR

This application is based on, and claims the benefit of, U.S. Provisional Application No. 60/043,047, filed Apr. 4, 1997, and entitled NON-INFECTIOUS, PROTEASE DEFECTIVE HIV PARTICLES AND NUCLEIC ACID MOLECULES ENCODING THEREFOR.

BACKGROUND OF THE INVENTION

This invention relates to human immunodeficiency viruses in general and, more specifically to non-infectious vaccines for the treatment of human immunodeficiency disease.

AIDS is a lethal disease caused by human immunodeficiency viruses HIV-1 and HIV-2. This disease is characterized by a long, latent asymptomatic phase. During this phase the HIV particles are suppressed by the body's immune defense system. The next phase of the disease occurs when the body's immune system is no longer able to suppress the viral particles. At this stage of the disease, the HIV viral particles attack and destroy a key component of the body's immune defense system called $CD4^+$ cells. Once these cells are destroyed, the third and final phase of the disease occurs. During this last phase, the body is extremely susceptible to infections by many different kinds of diseases. These so-called secondary infections are the cause of death in many AIDS patients.

One of the central mysteries about AIDS is why HIV particles can exist in the body for so long, yet the patient remains asymptomatic. As a corollary to this riddle, there is no certain explanation why the immune system suddenly fails to be effective against the particles, thus enabling the second phase of the disease.

One theory for the sudden onslaught of the HIV particles on the $CD4^+$ cells is that this onslaught is made by "defective" HIV particles. These new, defective particles are not recognized by the body's immune system. These defective particles have mutations in some of the key polypeptides of an HIV viral particle, yet somehow are still able to affect sufficient damage on the $CD4^+$ cells by means other than the classical invasion of the cells.

Surprisingly, non-infectious HIV particles produced by a cell called "L-2" fuse more efficiently than wild-type HIV with a subpopulation of $CD4^+$ cells. The enhanced fusion is caused by the 4-fold increased level of gp120, the two deletion mutations in gp120, altered conformational epitopes of gp120 and/or a combination of these factors, as well as mutant forms of Nef, gp41, protease, and Vpr, as discussed below. The fusion is far from the typical action of normal HIV infectious viral particles, in that it leads to the stimulation and release of Il-2R, Fas ligand and interferon-gamma 1 from a small subset of $CD4^+$ cells (Kameoka et al., *International Immunology* 9(10):1453–1462 (1997)). This occurs after L-2 particle fusion with these $CD4^+$ cells, a high percentage of uninfected, healthy neighboring $CD4^+$, as well as $CD8^+$ cells, are prematurely thrown into a programmed cell death cycle, ultimately resulting in apoptosis. Apoptosis is a natural process in most cells in the body, but only after such cells have become senescent. Fusion of L-2 particles with $CD4^+$ cells can also cause such cells to form multi-nucleated protoplasmic masses called "syncytia", which die shortly thereafter.

Thus, there exists a need to detect such defective HIV particles in the infected population; both for asymptomatic carriers, as well as for ARC (AIDS Related Complex) or AIDS patients. Furthermore, a need exists for prophylactic, immunogenic, and therapeutic agents for such defective particles, as well as polypeptides or fragments of polypeptides derived from the particles or their mutant nucleic acid sequences. This need exists due to the fact that mutations found in L-2 particles are normally produced in HIV infected individuals, so that development of immunity to them by natural or artificial means is a key to thwarting the pathogenic process leading to ARC and AIDS. This invention provides these advantages and more.

BRIEF DESCRIPTION OF THE DRAWINGS

FIG. 1 sets forth the mutations in the nucleotide sequences and deduced amino acid residues of the defective HIV-1 provirus in L-2 cells compared with those in MO/LAI and LAI cells. The portions of the nucleotide sequences of the relevant pol protease (prot.), vpr, env (gp120 and gp41), and nef gene regions in wild-type HIV-1 (LAI), as well as the proviruses of L-2 or MO/LAI, are shown in the upper part for each gene. The portions of the deduced amino acid sequences of Pol, Vpr, Env and Nef polypeptides setting forth the mutations are shown below the nucleotide sequences. The wild-type LAI control sequences are taken from previously reported sequences for HIV-1 (LAI), in GenBank. The sequences identical with those of wild-type LAI are indicated by dots. An asterisk (*) indicates the appearance of stop codons. For the upper part, a dash (–) indicates a deletion in nucleotide sequences. For the amino acid sequences represented in the lower part, a dash indicates sequences identical with the wild type HIV-1 (LAI) sequence. A hatchmark (#) indicates a deletion in deduced amino acid residues. Three pluses (+) indicates any three nucleotides coding for the corresponding amino acid shown in the deduced amino acid sequence.

FIG. 2 sets forth the primers used for PCR amplification of protease-defective HIV-1 provirus in L-2 cells. Nucleotide numbers are those of the HIV-1 molecular clone pNL432 (Adachl et al., *J. Virol,* 59:284–291 (1986)).

FIG. 3 sets forth the partial nucleic acid sequence of the mutated nef gene of the HIV-1 protease-defective provirus in the L-2 cell, where the individual bases that differ from the wild-type LAI HIV-1 virus in GenBank are encircled.

FIG. 4 sets forth the sequence of the truncated Nef polypeptide coded for by the mutated nef gene of the L-2 HIV-1 provirus. The encircled amino acids differ from the wild-type LAI HIV-1 virus amino acid sequence set forth in GenBank.

SUMMARY OF THE INVENTION

This invention is directed to nucleic acid molecules and fragments thereof containing mutations in certain genes of the HIV-1 virus, and the polypeptides and fragments thereof that are encoded by such mutated nucleic acid molecules, antibodies to such polypeptides, nucleic acid and antibody-based assays, as set forth below, as well as therapeutic uses of such antibodies. This invention is also directed to immunogens, and compositions of immunogens and adjuvants, containing such mutated HIV-1 viruses and in the production and use in therapeutic and prophylactic (immunogenic) methods and compositions.

DETAILED DESCRIPTION OF THE INVENTION

The invention is directed to the identification of mutations within pathologically important genes of the human immunodeficiency genome (HIV) which render viral particles non-infectious. The non-infectious phenotype of the viral particles can advantageously be used as a natural source of material for the production of immunogens for vaccination against or treatment of Acquired Immunodeficiency Syndrome (AIDS). The mutations identified within the various pathologically important genes can also be advantageously used to engineer new non-infectious viral particles for use as immunogens against essentially any type of HIV isolate.

In one embodiment, the invention is directed to the mutations discovered in various pathologically important genes of the non-infectious, protease-defective HIV-1 provirus harbored by L-2 cells. The partial sequences illustrating the nucleotide and amino acid changes caused by these mutations are set forth in FIGS. 1, 3 and 4.

The formation of syncytia and apoptosis of bystander T cells appear to be a mechanism of HIV-1-induced pathogenesis, leading to the diminution of T cells. (Amazon and Capon, *Immunol., Today,* 12:102–105 (1991); Malderelli et al., *J. Virology,* 69:6457–6465 (1995); and Sodroski et al., *Nature,* 322:470–474 (1996). It has been reported that subclones obtained from surviving cells after MT-4, a CD4 human T cell line, had been infected with wild-type LAI or infectious molecular clone pNLA32-derived viruses, were predominantly producers of infectious but less cytopathogenic virus particles (Yunoki et al., *Arch. Virol.,* 116:143–158 (1991); Nishino et al., *Arch. Virol.,* 120:181–192 (1991)). The provirus in these persistently infected cell clones carried mutations in accessory genes, such as vif, vpr, and vpu. (Nishino et al., *J. Gen. Virol.,* 75:2241–2251 (1994), and Kishi et al., *J. Virol.,* 69:7507–7518 (1995)). However, about 10% of the subclones produced above with LAI virus showed defective phenotypes even in essential gene products. In particular, one of these, named the L-2 cell clone, was a large-scale producer of protease-defective, gp120-containing noninfectious particles. (Ikuta et al., *J. Cancer Res.,* 78:118–123 (1988)).

Surprisingly, the protease-defective viral particles produced from the L-2 cell clone rapidly induce syncytium formation of uninfected T cells by virus-to-cell fusion (fusion from without), without the need for viral replication. (Ohki et al., *J. AIDS,* 4:1233–1240 (1991). In addition, the L-2 particles have a significantly higher (>fivefold) activity for apoptosis induction in primary peripheral blood T cells, as well as a certain subset of U937 cells when compared with soluble recombinant gp120 or the wild-type HIV-1 (LAI) strain (Kameoka et al., *Int. Immunol.,* 11:1687–1697 (1996); Kameoka et al., *J. Clin. Microbiol.,* 35:41–47 (1997)). Sodium dodecyl sulfate-polyacrylamide gel electrophoretic (SDS-PAGE) analysis demonstrates that the Gag precursor polypeptide in L-2 particles was not cleaved to mature Gag polypeptides and that the Env/Gag ratio in L-2 particles was about fourfold higher than that in HIV-1 (LAI) wild-type particles produced from persistently infected MOLT-cells (Yunoki et al., *Arch. Virol.,* 116:143–158 (1991); Kameoka et al. (1997) supra)).

"Substantially pure" when used to describe the state of the claimed nucleic acids, polypeptides or fragments thereof, is intended to mean that the claimed molecules are free of at least a portion of the contents associated with or occurring with the claimed nucleic acids, polypeptides or fragments thereof in the native environment.

As used herein, the term "substantially" or "substantially the same" when used in reference to a nucleotide or amino acid sequence is intended to mean that the nucleotide or amino acid sequence shows a considerable degree, amount or extent of sequence identity when compared to a reference sequence. Such considerable degree, amount or extent of sequence identity is further considered to be significant and meaningful and therefore exhibit characteristics which are definitively recognizable or known. Thus, a nucleotide sequence which is substantially the same nucleotide or amino acid sequence as a claimed sequence, refers to a sequence which exhibits characteristics that are definitively known or recognizable as representing the claimed nucleotide or amino acid sequence and minor modifications thereof.

In regard to substantially the same nucleotide sequences, such characteristics include for example, specific hybridization of a nucleotide sequence to a claimed nucleic acid or its compliment. Hybridization principles and methods for determining hybridization specificity are well established and are known by one skilled in the art. Such principles and methods can be found in, for example, Sambrook et al., *Molecular Cloning: A Laboratory Manual,* Cold Spring Harbor Laboratory, New York (1992), and in Ausubel et al., *Current Protocols in Molecular Biology,* John Wiley and Sons, Baltimore, Md. (1989). Thus, it is not necessary that two nucleic acids exhibit sequence identity to be substantially complimentary, only that they can specifically hybridize or be made to specifically hybridize without detectible cross reactivity with other similar sequences.

In regard to substantially the same amino acid sequence, such characteristics which are definitively recognizable or known include, for example, maintaining the biological function of the polypeptide or substitution of conservable amino acid residues. It is understood that limited modifications may be made without destroying the biological function of the claimed polypeptides or fragments thereof, and that only a portion of the entire primary structure can be required in order to effect activity. For example, the claimed polypeptides of the invention have an amino acid sequence substantially similar to those indicated for the L-2 polypeptides shown in FIGS. 1 or 4, but minor modifications of these sequences which do not destroy their activity also fall within the definition of the polypeptides claimed as such. Moreover, fragments of the sequences of the L-2 polypeptides shown in FIGS. 1 and 4, are similarly included within the definition. It is understood that minor modifications of primary amino acid sequence may result in polypeptides which have substantially equivalent or enhanced function as compared to the sequences of the L-2 polypeptides set forth in FIGS. 1 and 4. These modifications can be deliberate, as through site-directed mutagenesis, or may be accidental such as through mutation in hosts which produce the claimed polypeptides. All of these modifications are included as long as the biological functions are retained.

As used herein, the term "fragment" when used in reference to a nucleic acid encoding the claimed polypeptides is intended to mean a nucleic acid having substantially the same sequence as a portion of a nucleic acid encoding the claimed Pol protease, Nef, Env gp41, Env gp120 or Vpr polypeptides or fragments thereof. The nucleic acid fragment is sufficient in length and sequence to selectively hybridize to a Pol protease, Nef, Env gp41, gp120 or Vpr encoding nucleic acid or a nucleotide sequence that is complimentary to a Pol protease, Nef, Env gp41, gp120 or Vpr encoding nucleic acid. Therefore, fragment is intended to include primers for sequencing and polymerase chain reaction (PCR) as well as probes for nucleic acid blot or solution hybridization.

As used herein, the term "functional fragment" when used in reference to a Pol protease, Nef, Env gp41, gp120 or Vpr polypeptide is intended to refer to a portion of a Pol protease, Nef, Env gp41, gp120 or Vpr polypeptide which still retains some or all or the apoptotic inducing activity of the L2 particles containing one or more of these polypeptides as described herein. The term is also intended to include polypeptides that include, for example, modified forms of naturally occurring amino acids such as D-steroisomers, non-naturally occurring amino acids, amino acid analogues and mimics so long as such polypeptides retain functional activity as defined above.

The HIV-1 provirus from L-2 cells has been analyzed with respect to genetic mutations that result in non-infectious HIV particles. Genes of HIV-1 provirus from L-2 cells have been isolated and sequenced and compared to the wild type HIV-1 MO/LAI and LAI isolates. Various mutations have been observed in several viral genes encoding viral polypeptides, including the nef, env, pol and vpr genes.

One aspect of the instant invention is a substantially pure nucleic acid molecule encoding a mutant HIV-1 Nef protein, containing the encircled L-2 mutations set forth as SEQ ID NO:45 (FIG. 3), and any fragments of such a nucleic acid molecule containing at least one of the encircled L-2 mutations which can be used to specifically detect the mutated nucleic acid or protein.

The nef gene of HIV-1 provirus from L-2 cells was compared to the wild type HIV-1 in MO/LAI and LAI isolates GenBank accession No. K02013. Several mutations in the nef gene compared to the wild type HIV-1 nef gene sequence were observed. One mutation is the substitution of A for G at nucleotide 169 of the nef gene (SEQ ID NO:47). This mutation results in a stop codon at amino acid residue 57 such that the Nef polypeptide is truncated and contains amino acids 1 through 56 (SEQ ID NO:48).

The invention provides a substantially pure nucleic acid molecule or fragment thereof that encodes a truncated Nef protein comprising a nucleic acid sequence that encodes substantially the same sequence of amino acid residues 1 through 56 of an HIV-1 Nef polypeptide.

Another mutation found in the nef gene of HIV-1 provirus from L-2 cells is the substitution of G for the A at nucleotide 43 of the wild type nef gene. This mutation changes Thr at amino acid residue 15 of the Nef polypeptide to Ala. An additional mutation found in the nef gene of HIV-1 provirus from L-2 cells is the substitution of A for the G at nucleotide 56 of the wild type nef gene. This mutation changes Arg at amino acid residue 19 of the Nef polypeptide to Lys.

Additional mutations of the nef gene of HIV-1 provirus from L-2 cells were found. One of these mutations is the substitution of T for the C at nucleotide 98 of the wild type nef gene. This mutation changes Ala at amino acid residue 33 of the Nef polypeptide to Val. Still another of these mutations is the substitution of A for the C at nucleotide 161 of the wild type nef gene. This mutation changes Ala at amino acid residue 54 of the Nef polypeptide to Asp.

An additional mutation found in the nef gene of HIV-1 provirus from L-2 cells is the substitution of A for the G at nucleotide 111 of the wild type nef gene. This mutation results in no change in the amino acid at residue 37 of the encoded Nef polypeptide since the nucleotide substitution occurs in the third position of the codon for Leu and all nucleotide substitutions at this position would encode for Leu. Therefore, nucleotide 111 of the nef gene can be any of the four nucleotides.

The invention also provides a substantially pure nucleic acid or fragment thereof that encodes a Nef polypeptide comprising a nucleotide sequence that encodes substantially the same amino acid sequence of an HIV-1 Nef polypeptide containing Ala at amino acid residue 15. The invention additionally provides a substantially pure nucleic acid or fragment thereof that encodes a Nef polypeptide comprising a nucleotide sequence that encodes substantially the same amino acid sequence of an HIV-1 Nef polypeptide containing Lys at amino acid residue 19.

The invention further provides a substantially pure nucleic acid or fragment thereof that encodes a Nef polypeptide comprising a nucleotide sequence that encodes substantially the same amino acid sequence of an HIV-1 Nef polypeptide containing Val at amino acid residue 33. The invention also provides a substantially pure nucleic acid or fragment thereof that encodes a Nef polypeptide comprising a nucleotide sequence that encodes substantially the same amino acid sequence of an HIV-1 Nef polypeptide containing Asp at amino acid residue 54.

The nucleotide substitutions and amino acid mutations found in the nef gene of HIV-1 provirus from L-2 cells and the encoded Nef polypeptide are shown in FIGS. 3 and 4, respectively.

A second aspect of the instant invention is a substantially pure nucleic acid molecule encoding a mutated HIV-1 env gp41 protein containing the L-2 mutation set forth in SEQ ID NO:29 (FIG. 1) and any fragment of such nucleic acid molecule containing the mutation which can be used to specifically detect the mutated nucleic acid or protein.

A mutation in the L-2 cell derived HIV-1 provirus env gene encoding the Env gp41 polypeptide has also been identified. The mutation is the substitution of G for the A at nucleotide 7781 (nucleotide 1979 in FIG. 1) in a wild type env gene. This mutation changes Lys at amino acid residue 660 of the Env gp41 polypeptide to Arg.

The invention also provides a substantially pure nucleic acid or fragment thereof that encodes an Env gp41 polypeptide comprising a nucleotide sequence that encodes substantially the same amino acid sequence of an HIV-1 Env gp41 polypeptide containing Arg at amino acid residue 660.

A third aspect of the instant invention is a substantially pure nucleic acid molecule encoding a mutated HIV-1 pol protease protein containing the L-2 mutation set forth in SEQ ID NO:5 (FIG. 1) and any fragment of such nucleic acid molecule containing the mutation which can be used to specifically detect the mutated nucleic acid or protein.

A mutation in the L-2 cell derived HIV-1 provirus pol protease gene encoding the pol protease polypeptide has also been identified. The mutation is the insertion of T after the A at nucleotide 41 in wild type pol protease gene. This mutation results in a frameshift and the appearance of a stop codon at amino acid residue 30 of the Pol protease polypeptide. This results in a 29 amino acid Pol protease polypeptide with the carboxyl-terminal amino acid sequence AsnAspArgGlyAlaThrLysGlySerSerIleArgTyrArgSerArg (SEQ ID NO:6) starting at amino acid residue 14.

The invention additionally provides a substantially pure nucleic acid or fragment thereof that encodes a Pol protease polypeptide comprising a nucleotide sequence that encodes substantially the same sequence of amino acid residues 1 through 13 of an HIV-1 Pol protease polypeptide fused at the carboxyl-terminus to substantially the same amino acid sequence AsnAspArgGlyAlaThrLysGlySerSerIleArgTyrArgSerArg (SEQ ID NO:6).

A fourth aspect of the invention is directed to a substantially pure nucleic acid molecule encoding a mutant HIV-1 gp120 protein containing the L-2 mutations set forth in SEQ ID NOS:17 and 23 (FIG. 1), and any fragment of said nucleic acid containing one or more of the L-2 mutations which can be used to specifically detect the mutated nucleic acid or protein.

Mutations in the L-2 cell derived HIV-1 provirus env gene encoding the Env gp120 polypeptide have also been identified. A mutant Env gp120 found in HIV-1 provirus from L-2 cells has a substitution of Arg for the Ser at amino acid residue 143, substitution of Ile for the Met at position 153 and deletion of eight amino acids, from 144 through 151, of the wild type HIV-1 from LAI cells as well as substitution of Val for the Ile at amino acid residue 187 and deletion of two amino acids, 192 and 193, of the wild type HIV-1 from LAI cells. The substitution of Arg at amino acid position 143 occurred due to nucleotide substitutions that changed the codon for Ser to the codon for Arg. Any mutation that results in changing the nucleotides encoding Ser 143 (nucleotides 427 through 429) to Arg can be used in the nucleic acids of the invention. For example, nucleotides 427 through 429, AGT, can be substituted with nucleotides that result in a codon for Arg, such as substitution of A for the T at nucleotide 429, substitution of G for the T at nucleotide 429, substitution of C for the A at nucleotide 427, substitution of C for the A at position 427 combined with substitution of C for the T at nucleotide 429, substitution of C for the A at position 427 combined with the substitution of A for the T at nucleotide 429, and substitution of C for the A at position 427 combined with the substitution of G for the T at nucleotide 429, all of which result in substitution of Arg for Ser at amino acid position 143. The substitution of Ile for Met at amino acid residue 153 results from substitution of A for the G at nucleotide 459. The substitution of Val for Ile at amino acid residue 187 results from substitution of G for A at nucleotide 559. This mutant Env gp120 mutant is identical to a Env gp120 mutant found in HIV-1 from MO/LAI (see FIG. 1).

The invention also provides a substantially pure nucleic acid or fragment thereof that encodes an Env gp120 polypeptide comprising a nucleotide sequence that encodes substantially the same amino acid sequence of an HIV-1 Env gp1120 polypeptide containing Arg at amino acid residue 143, Ile at amino acid residue 153, and Val at the amino acid residue corresponding to amino acid residue 187 of a wild type HIV-1 Env gp120 polypeptide and absent amino acid residues corresponding to amino acid residues 144 through 151 and 192 through 193 of a wild type HIV-1 Env gp120 polypeptide.

A fifth aspect of the invention is directed to a substantially pure nucleic acid molecule encoding a mutant HIV-1 Vpr protein containing the L-2 mutation set forth in SEQ ID NO:11 (FIG. 1), and any fragment of such a nucleic acid molecule containing the L-2 mutation which can be used to specifically detect the mutated nucleic acid or protein.

A mutation in the L-2 cell derived HIV-1 provirus vpr gene encoding the Vpr polypeptide has also been identified. The mutation is the substitution of A for the G at nucleotide 5194 (nucleotide 54 in FIG. 1) in a wild type vpr gene. This mutation introduces a stop codon at amino acid residue 18 such that the vpr gene encodes a truncated Vpr polypeptide containing amino acid residues 1 through 17.

The invention also provides a substantially pure nucleic acid or fragment thereof that encodes a Vpr polypeptide comprising a nucleotide sequence that encodes substantially the same sequence of amino acid residues 1 through 17 of an HIV-1 Vpr polypeptide.

In addition to the nucleic acids described above encoding individual Nef, Env gp41, Pol protease, Env gp120 and Vpr polypeptide mutants, the invention also provides substantially purified nucleic acids encoding combinations of these mutant polypeptides. In one embodiment, any of the mutations in an individual polypeptide can be used alone or in combination with one or more additional mutations in the same polypeptide. Thus, the invention provides a substantially pure nucleic acid or fragment thereof that encodes a HIV-1 polypeptide having one or more of the mutations described above.

For example, a nucleic acid encoding a Nef polypeptide can include the deletion mutant, which encodes amino acid residues 1 through 56 of the Nef polypeptide, and any combination of one or more of the amino acid substitutions. The invention provides a nucleic acid encoding the truncated Nef polypeptide containing amino acid residues 1 through 56 and Ala at amino acid residue 15. A nucleic acid can also encode the truncated Nef polypeptide with Lys at amino acid residue 19. Similarly, any of the amino acid substitution mutations in the Nef polypeptide described above can be combined with the truncated Nef polypeptide. Alternatively, any of the amino acid substitution mutations can be combined with each other in the full length Nef polypeptide or a fragment thereof.

The invention thus provides a substantially pure nucleic acid or fragment thereof that encodes at least one of the mutations described above and can, where more than one mutation has been described in an individual polypeptide, contain any combination of two or more mutations, including as many as all of the mutations described for an individual polypeptide. An example of such a nucleic acid encoding an individual polypeptide having multiple mutations is shown in FIG. 3 (SEQ ID NO:45).

In another example of a nucleic acid encoding an individual polypeptide for which multiple mutations have been identified, a nucleic acid encoding Env gp120 can contain the deletion of up to eight amino acids of amino acid residues 144 through 151. A nucleic acid encoding Env gp120 can also contain the deletion of one or two amino acids of amino acid residues 192 and 193. A nucleic acid encoding Env gp120 can additionally contain the combination of deletion of up to eight amino acids of amino acid residues 144 through 151 and deletion of one or two amino acids of amino acid residues 192 and 193. Additionally, any combination of one or both of the deletion mutations can be combined with Arg at amino acid residue 143. The combination of one or both of the deletion mutations can also be combined with Ile at amino acid residue 153. Also, the combination of one or both of the deletion mutations can be combined with Val at amino acid residue 187. Additionally, the combination of one or both of the deletion mutations can be combined with one or two of the single amino acid substitutions.

In another embodiment in which nucleic acids encode a combination of amino acid mutations of polypeptides, the invention also provides a substantially pure nucleic acid or fragment thereof that encodes more than one polypeptide containing at least one mutation. A nucleic acid of the invention can therefore encode any one or more of the polypeptides selected from the group consisting of Nef, Env gp41, Pol protease, Env gp120 and Vpr polypeptides so long as the encoded polypeptides contain at least one of the mutations described above. For example, a substantially pure nucleic acid can encode a truncated Nef polypeptide containing amino acid residues 1 through 56 and Env gp41 containing Arg at amino acid residue 660. In another embodiment, a substantially pure nucleic acid can encode three or more of the polypeptides selected from the group consisting of Nef, Env gp41, Pol protease, Env gp120 and Vpr polypeptides, up to and including all of these polypeptides so long as at least one of the amino acid mutations described above is encoded by the nucleic acid. For example, a substantially pure nucleic acid can encode all of the polypeptides Nef, Env gp41, Pol protease, Env gp 120 and Vpr polypeptides having all of the amino acid mutations described above.

Further aspects of this invention are the substantially pure polypeptides or fragments thereof that are encoded by any of the above nucleic acid molecules. In one aspect of the invention, the substantially pure polypeptides or fragments thereof can be used to raise antibodies which are specific to the mutated proteins.

The invention provides a substantially pure HIV-1 polypeptide or a fragment thereof selected from the group of polypeptides consisting of Nef, Env gp41, Pol protease, Env gp120 and Vpr, wherein the HIV-1 polypeptide contains at least one of the mutations found in HIV-1 provirus from L-2 cells. Such mutations found in HIV-1 provirus from L-2 cells are described above.

In one embodiment, the invention provides Nef polypeptides having one or more mutations in the Nef polypeptide of a HIV-1 provirus from L-2 cells. For example, the invention provides a substantially pure Nef polypeptide or fragment thereof comprising substantially the same sequence of amino acid residues 1 through 56 of a HIV-1 Nef polypeptide. The invention also provides a substantially pure Nef polypeptide or fragment thereof comprising substantially the same amino acid sequence of an HIV-1 Nef polypeptide containing Ala at amino acid residue 15. The invention additionally provides a substantially pure Nef polypeptide or fragment thereof comprising substantially the same amino acid sequence of an HIV-1 Nef polypeptide containing Lys at amino acid residue 19.

The invention further provides a substantially pure Nef polypeptide or fragment thereof comprising substantially the same amino acid sequence of an HIV-1 Nef polypeptide containing Val at amino acid residue 33. The invention also provides a substantially pure Nef polypeptide or fragment thereof comprising substantially the same amino acid sequence of an HIV-1 Nef polypeptide containing Asp at amino acid residue 54.

In addition to the Nef polypeptides having the individual mutations described above, the invention also provides a substantially pure Nef polypeptide or fragment thereof having any combination of one or more of the Nef polypeptide mutations. For example, the invention provides Nef polypeptides having one or more of the amino acid substitution mutations described above in the full length Nef polypeptide. Furthermore the invention provides a truncated Nef polypeptide and a combination of one or more of the amino acid substitution mutations described above. For example, the invention provides a truncated Nef polypeptide containing amino acids 1 through 56 and Ala at amino acid residue 15. Additionally, the invention provides a truncated Nef polypeptide containing amino acids 1 through 56 and Lys at amino acid residue 19. Further provided is a truncated Nef polypeptide containing amino acids 1 through 56 and Val at amino acid residue 33. Also provided is a truncated Nef polypeptide containing amino acids 1 through 56 and Asp at amino acid residue 54.

In addition to the Nef polypeptide truncation mutants combined with a single amino acid substitution mutation, the invention also provides a truncated Nef polypeptide containing amino acids 1 through 56 and two or more of the amino acid substitution mutations described above. For example, the Nef polypeptide can contain amino acid residues 1 through 56 and Asp at amino acid residue as well as Val at amino acid residue 33. Furthermore, the invention provides a truncated Nef polypeptide containing amino acid residues 1 through 56 as well as Ala at amino acid residue 15, Lys at amino acid residue 19, Val at amino acid residue 33, and Asp at amino acid residue 54. Therefore, one aspect of the instant invention is the truncated HIV-1 Nef protein containing the amino acid substitutions set forth in SEQ ID NO:46 (FIG. 4). The amino acid sequence of such a Nef polypeptide combining all of the Nef polypeptide mutations found in HIV-1 provirus from L-2 cells is shown in FIG. 4 (SEQ ID NO:46).

The invention also provides a substantially pure Env gp41 polypeptide or fragment thereof comprising substantially the same amino acid sequence of an HIV-1 Env gp41 polypeptide containing Arg at amino acid residue 660. The invention additionally provides a substantially pure Pol protease polypeptide or fragment thereof comprising substantially the same sequence of amino acid residues 1 through 13 of an HIV-1 Pol protease polypeptide fused at the carboxyl-terminus to substantially the same amino acid sequence as AsnAspArgGlyAlaThrLysGlySerSerIleArgTyrArgSerArg (SEQ ID NO:6).

The invention also provides a substantially pure Env gp120 polypeptide or fragment thereof comprising substantially the same amino acid sequence of an HIV-1 Env gp120 polypeptide containing Arg at amino acid residue 143, Ile at amino acid residue 153, and Val at the amino acid residue corresponding to amino acid residue 187 of a wild type HIV-1 Env gp120 polypeptide and absent amino acid residues corresponding to amino acid residues 144 through 151 and 192 through 193 of a wild type HIV-1 Env gp120 polypeptide.

The invention also provides a substantially pure Env gp120 polypeptide comprising substantially the same amino acid sequence of an Env gp120 polypeptide with deletion of at least one and up to eight amino acids of amino acid residues 144 through 151. The invention additionally provides a substantially pure Env gp120 polypeptide comprising substantially the same amino acid sequence of an Env gp120 polypeptide with deletion of one or both of amino acid residues 192 and 193.

Additional Env gp120 polypeptides are also provided in the present invention. For example, the invention provides an Env gp120 polypeptide comprising deletion of at least one and up to eight amino acids of amino acid residues 144 through 151 and deletion of one or both of amino acid residues 192 and 193. Additionally, the invention provides Env gp120 polypeptides comprising deletion of at least one and up to eight amino acids of amino acid residues 144 through 151 and deletion of one or both of amino acid residues 192 and 193 as well as Arg at amino acid residue 143. The invention also provides Env gp120 polypeptides comprising deletion of at least one and up to eight amino acids of amino acid residues 144 through 151 and deletion of one or both of amino acid residues 192 and 193 as well as Ile at amino acid residue 153. Also, the invention provides Env gp120 polypeptides comprising deletion of at least one and up to eight amino acids of amino acid residues 144 through 151 and deletion of one or both of amino acid residues 192 and 193 as well as Val at amino acid residue 187.

The invention further provides Env gp120 polypeptides comprising deletion of at least one and up to eight amino acids of amino acid residues 144 through 151 and deletion of one or both of amino acid residues 192 and 193 as well as two of the amino acid substitution mutations. For example, the invention provides Env gp120 polypeptides comprising deletion of at least one and up to eight amino acids of amino acid residues 144 through 151 and deletion of one or both of amino acid residues 192 and 193 as well as Arg at amino acid residue 143 and Ile at amino acid residue 153. The invention also provides Env gp120 polypeptides comprising deletion of at least one and up to eight amino acids of amino acid residues 144 through 151 and deletion of one or both of amino acid residues 192 and 193 as well as Arg at amino acid residue 143 and Val at amino acid residue 187. The invention further provides Env gp120 polypeptides comprising deletion of at least one and up to eight amino acids of amino acid residues 144 through 151 and deletion of one or both of amino acid residues 192 and 193 as well as Ile at amino acid residue 153 and Val at amino acid residue 187.

The invention also provides a substantially pure Vpr polypeptide or fragment thereof comprising substantially the same sequence of amino acid residues 1 through 17 of an HIV-1 Vpr polypeptide.

As discussed above for Nef polypeptide and Env gp120, any of the mutations in an individual polypeptide can be used alone or in combination with one or more additional mutations in the same polypeptide. Thus, the invention provides a substantially pure HIV-1 polypeptide or fragment thereof selected from the group consisting of Nef, Env gp41, Pol protease, Env gp120 and Vpr that contain two or more of the mutations described above in a single individual polypeptide.

The invention thus provides a substantially pure HIV-1 polypeptide or fragment thereof selected from the group of polypeptides consisting of Nef, Env gp41, Pol protease, Env gp120 and Vpr, wherein the HIV-1 polypeptide or fragment thereof comprises at least one of the mutations described above and can, where more than one mutation has been described in an individual polypeptide, comprise any combination of two or more mutations, including as many as all of the mutations described for an individual polypeptide.

Any combination of one or more of the HIV-1 polypeptides containing any combination of one or more of the mutations described above can be expressed together as desired. The choice of combination of polypeptides and the combination of mutations in the polypeptides depends on the needs of the investigator.

The invention also provides nucleic acids encoding substantially the same amino acid sequence of the mutant HIV-1 polypeptides described above. Any nucleic acid that encodes any combination of single mutations in a polypeptide, multiple mutations in a polypeptide or a combination of two or more polypeptides of the invention are also provided.

The genes of HIV-1 provirus from L-2 cells described above were isolated using PCR amplification as described in Example I. However, the nucleic acid molecules described above can be isolated from L-2 cells by any of a variety of methods well known in the art. For example, in addition to PCR amplification of nucleic acids, other methods well known in the art regarding cloning of DNA from an organism can be used to isolate HIV-1 provirus DNA (Sambrook et al., Eds., *Molecular Cloning: A Laboratory Manual,* 2nd Ed., Cold Springs Harbor Laboratory Press (1989), which is herein incorporated by reference). Furthermore, the nucleic acids of the invention, which are set forth above, can be synthesized by chemical means (See, Blackburn and Gait, Eds., *Nucleic Acids in Chemistry and Biology,* 2nd Ed., Oxford University Press (1996), which is herein incorporated by reference).

The proteins and peptides encoded by said nucleic acids can be isolated and purified from L-2 viral particles (see, for example, Deutscher, Ed., *Methods in Enzymology: Guide to Protein Purification,* Vol. 182, Academic Press, Inc., San Diego, Calif. (1990), herein incorporated by reference), or chemically synthesized or expressed in a recombinant organism by methods well known in the art, such as Stewart and Young, Eds., *Solid Phase Peptide Synthesis,* 2nd Ed., Pierce Chemical Company (1984); Kriegler, M., Ed., *Gene Transfer and Expression: A Laboratory Manual,* Stockton Press, New York, N.Y. (1990); and Jones, J., Ed., *The Chemical Synthesis of Peptides,* Oxford University Press, Oxford (1994), all of which are herein incorporated by reference. For example, the substantially pure nucleic acids of the invention can be expressed recombinantly in bacterial or eukaryotic cells and subsequently purified.

As non-infectious particles, the L-2 viral particles can be used as immunogens to induce a host immune response against an HIV infection. More specifically, the immunogens can be used for the prevention or reduction of apoptotic cell lysis caused by HIV infection.

The L-2 viral particles can be produced by methods well known in the art. For example, non-infectious viral particles can be produced by growing L-2 cells in culture under conditions such that protease-defective L-2 HIV particles are produced. Such particles are then separated from L-2 cells by, for example, centrifugation of the L-2 cell supernatant and recovering the particles in the pellet. Such methods are described further below in the Examples as well as in, for example, Ohki et al., *J. Acquired Immun. Def. Syn.* 4:1233–1240 (1991).

The non-infectious L-2 viral particles can be used directly as an immunogen or, alternatively, can be further treated to ensure multiple, additional levels of viral particle inactivation. Additional inactivation treatment is a precautionary measure to provide further confidence and safety levels against possible commination of non-L-2 HIV viral particles. Methods of viral particle inactivation are well known in the art and include, for example, treatment with gamma-radiation, beta-propiolactone and gluaraldehye. These methods are described further below in the Examples. Moreover, the production and use of immunogens is taught, for example, in Salk et al., U.S. Pat. No. 5,256,767, issued Oct. 26, 1993. Therefore, the invention provides an immunogen consisting of non-infectious, protease-defective particles produced by L-2 cells. The invention also provides inactivated, protease-defective particles produced by L-2 cells. The non-infectious, protease-defective particles can also be produced by non-L-2 cells which harbor the L-2 provirus genome.

As described above, the L-2 viral particles contain a number of mutations which render the particles non-infectious. These mutations can be advantageously exploited to engineer a variety of non-infectious viral particles as specific immunogens against preselected types of HIV viruses. For example, it is not necessary to have all of the mutations described herein for the particle to be non-infectious and therefore useful as an immunogen. Instead, immunologically effective immunogens can be prepared from modified forms of the L-2 viral particles containing less than all of the mutations described herein so long as the modified L-2 viral particle contains a mutation that renders the particle non-infectious. Such mutations can be, for example, any one of the mutations identified in the Pol protease, Nef, or Env gp41, for example. These mutations can be combined with the L-2 Env gp120 polypeptide or the L-2 Env gp120 mutants described herein to produce non-infectious viral particles for vaccinating against HIV. Other mutant polypeptides such as the L-2 Vpr or the L-2 Vpr mutants described herein can also be included within the viral particles to augment the non-infectious phenotype of the modified L-2 viral particles. Those skilled in the art will know or can determine which mutation or combination of mutations are sufficient to render the particle non-infections given the mutant sequences and teachings described herein.

Alternatively, the L-2 mutations identified in the Pol protease, Nef, or Env gp41 polypeptides can be combined with Env gp120 polypeptides from other HIV virus subtypes, or clades, to produce non-infectious viral particles. These particles can similarly be used as vaccines against the various HIV clades. For example, there are two primary groups of HIV clades, termed M and O, which characterize the infective phenotype of the virus. For group M, there are eight clades (A through J). The L-2 viral particles are characterized as being within the B clade of Group M, Betts et al., J. Virology 71:8909–8911 (1997).

The L-2 viral particle are characterized as being within the O clade having subgroup E. Substituting Env gp120 derived from different clades or clade subgroups into non-infectious L-2 viral particles will render a modified L-2 particle specific for the substituted Env gp120 clade. These clade-specific, modified L-2 particles can then be used as immunogens for the prevention and treatment of an HIV infection.

As with the modified L-2 viral particles described above, immunogenically effective immunogens can be prepared from the clade-specific forms of the modified L-2 viral particles that contain less than all of the L-2 mutations described herein so long as the particles contain at least one of the mutations that renders the particle non-infectious. Such mutations can be, for example, any one of the mutations identified in the Pol protease, Nef, or Env gp41, for example. Additionally, the mutations described in the Vpr protein can be optionally incorporated. Those skilled in the art will know or can determine which mutation or combination of mutations are sufficient to render the clade-specific viral particles non-infections given the mutant sequences and teachings described herein.

Production of the modified L-2 particles or the modified, clade-specific particles described above can be performed using methods well known in the art given the L-2 nucleotide and amino acid sequences and the teachings described herein. Such methods can include, for example, the construction and expression of recombinant modified L-2 genomes so as to contain a desired combination of the L-2 mutations which confer the non-infectious phenotype. The construction of such desired combinations can be performed by, for example, site directed mutagenesis or by polymerase chain reaction (PCR) using mutagenic primers. Other well known methods exist in the art and can similarly be used to generate the desired combination of L-2 mutations within to produce a modified L-2 genome or a modified, clade specific genome. Once produced, the genomes can be stably introduced into compatible cells, such as T cells, to harbor the provirus and effect the production of the modified viral particles. Such methods are well known in the art and can be found described in, for example, Sambrook et al., Eds., *Molecular Cloning: A Laboratory Manual*, 2nd Ed., Cold Spring Harbor Laboratory Press (1989), and Ausubel et al., Eds., *Current Protocols in Molecular Biology*, John Wiley & Sons, (1987). The non-infectious, modified L-2 particles, or the non-infectious, modified particles that exhibit clade-specific phenotypes can be isolated and used directly as immunogens or be subjected to further inactivation procedures as described above prior to use as immunogens for the prevention or treatment of apoptotic cell lysis mediated by HIV.

Specific examples of non-infectious, modified L-2 viral particles include particles containing at least an expressible Nef or Pol protease mutant as described previously. For example, the Nef mutant can contain the stop codon at position 57 and/or contain one or more of the nucleotide and corresponding amino acid mutations set forth in FIGS. 3 and 4, (SEQ ID NOS:45 and 46, respectively). The Pol protease mutant can contain one or more of the nucleotide and corresponding amino acid mutations set forth in FIG. 1 (SEQ ID NO:5 and 6, respectively). Any of the Nef or Pol protease mutants can additionally be combined with the various Vpr, Env gp41 or Env gp120 mutants previously describe to generate a non-infectious, modified L-2 viral particle of the invention. Similarly, such mutations can be constructed with non-L-2 Env gp120 polypeptides to produce non-infectious, modified L-2 particles that are clade specific.

Any of the previously described non-infectious L-2 viral particle immunogens, including modified forms and clade-specific forms, can additionally be combined with other HIV immunogens to further augment an immune response directed to HIV. Additional HIV immunogens can include, for example, inactivated forms of the virus, virus which is devoid of its outer envelope proteins, as well as soluble HIV polypeptides or fragments thereof. These additional HIV immunogens that can be combined with the non-infectious L-2 particles and modified forms thereof, can be derived from HIV-1, HIV-2 or both, for example. Such combined immunogens can similarly be formulated in an adjuvant for administration. Immunogens for the induction of an immune response against HIV are well known in the art. A specific example of an immunogen which is devoid of the Env gp120 polypeptide is described, for example, in Salk et al., supra.

Therefore, the invention provides a method for the reduction or prevention of apoptotic cell lysis mediated by HIV. The method consists of administration of a non-infectious L-2 particle or non-infectious modified L-2 particle to a human who is either seropositive or seronegative for HIV, and particularly in those patients where the apoptotic lysis is induced by protease-defective particles. Additionally, the invention provides for methods of stimulating the immune system of a human. Such a method would comprise administering one of the above non-infectious L-2 particle or modified L-2 particle immunogens, or a composition including such immunogens in an immunologically effective amount to a human. Again, the human could be seronegative or seropositive for HIV.

The non-infectious immunogens of the invention are administered to a host exhibiting or at risk of exhibiting an autoimmune response. Definite clinical diagnosis of AIDS or AIDS related complex (ARC) warrants the administration of the relevant immunogen. Prophylactic applications are warranted where an HIV infection precedes the onset of overt clinical disease or where the individual has been at risk of exposure to the virus. Thus, individuals with any history of infection or predicted to be at risk by reliable prognostic indicators can be treated prophylactically to interdict immunodeficiency mechanisms prior to their onset.

The non-infectious immunogens of the invention can be administered in many possible formulations, including pharmaceutically acceptable mediums. The immunogens can include or be administered in conjunction with an adjuvant, of which several are known to those skilled in the art. After initial immunization with the non-infectious immunogen, further boosters can additionally be provided. The non-infectious immunogens are administered by conventional methods, in dosages which are sufficient to elicit an immunological response. Such dosages are known and also can be easily determined by those skilled in the art.

Briefly, individuals who are candidates for immunization can be effectively treated by active immunotherapy using a non-infectious immunogen prepared from the L2-viral particles or modified forms thereof. The dose is selected so as to be immunologically effective, and is generally between about 1 to about 100 μg of protein, more preferably about 30 μg of protein.

Active immunization is implemented and preferably repeated once at a minimum interval of at least 90 days, although additional boosts may be appropriate according to changes in the immunocompetence level, based, for example, on a decline in antibodies to HIV gene products other than outer envelope proteins. Such immunization is preferably accomplished initially by intramuscular injection followed by intradermal injection, although any combination of intradermal and intramuscular injections may be used.

Preferably, the immunoresponsiveness or immunocompetence of the seropositive individual is determined prior to immunization in order to determine an appropriate course of therapy. As a method of such determination, individuals' sera can be screened for the presence of antibodies to p24 (as by means of ELISA), for TRI antibody and/or for the level of $T_4$ cells by methods well known in the art. Individuals exhibiting indicators of low immunocompetence, such as low p24 or RTI antibody titers or low numbers of $T_4$ cells, are appropriate candidates for active immunotherapy. Additionally, active immunotherapy can be combined with other therapies known in the art including, for example, passive immunotherapy.

Seronegative individuals can be vaccinated in order to induce immunoprotective factors to prevent infection. Preferably, the vaccine is administered initially by intramuscular injection followed by a booster injection given either intramuscularly or intradermally. A physiologically effective dose, preferably in the range of 1 to 100 μg and more preferably about 30 μg of immunogen is provided per dose. The vaccine can be administered in conjunction with an adjuvant, such as a water-in-oil type adjuvant. Various appropriate adjuvants are well known in the art as reviewed by Warren and Chedid, *CRC Critical Reviews in Immunology* 8:83 (1988).

These methods as well as other modes of administration are well known in the art and can be used for the prevention or treatment of an HIV infection using the non-infectious immunogens described herein.

The nucleic acid molecules discussed above can be used as nucleic acid probes or standards in either diagnostic or in PCR procedures. Such diagnostic methods can be used to detect the previously described mutant DNA sequences in cells and extracellular fluids. Methods of detection by hybridization with nucleic acid probes are well known in the art and are described in, for example, Hames and Higgins, Eds., *Nucleic Acid Hybridisation: A Practical Approach*, Oxford University Press, Oxford (1991), and Innis et al., Eds., *PCR Protocols: A Guide to Methods and Applications*, Academic Press, Inc. (1990). Various formats known in the art can be used for detection of L-2 specific mutations by nucleic acid hybridization. The choice of such formats will vary depending on the particular application and need of the diagnostic procedure. Formats include, for example, solid-phase hybridization and solution hybridization. Specific examples of solid-phase hybridization formats for diagnostic procedures include the use of diagnostic chips containing two-dimentional arrays of oligonucleotides, multi-well formats such as an ELISA and blot hybridization procedures. Such formats and various permutations thereof are well known in the art.

Similarly, the polypeptides above could be used as assay standards in immunoassays kits, and could be employed to raise antibodies for immunoassays to detect the above mutated polypeptides and organisms containing them. Methods for raising monoclonal and polyclonal antibodies specific to such polypeptides are well known in the art. (See, for example, Harlow and Lane, Eds., *Antibodies: A Laboratory Manual,* Cold Spring Harbor Laboratory (1988). Moreover, the production of monoclonal antibodies is described in detail in U.S. Pat. Nos. RE 32011 and 4,411,993. Antibodies to L-2 mutant polypeptides can additionally be generated using combinatorial methods well known in the art. Such methods include the generation and screening of recombinant antibody library repertoires for antibodies specific to an antigen of interest, including any of the L-2 mutant polypeptides described herein (see, for example, Huse et al., *Science* 246:1275–1281 (1989)). Monoclonal antibodies specific for the L-2 polypeptide described herein can additionally be modified by recombinant methods known in the art to incorporate human antibody framework sequences. Such methods are well known in the art and are described in, for example, U.S. Pat. No. 5,585,089 to Queen et al.

Once suitable antibodies or binding proteins have been obtained, they may be isolated or purified by many techniques well known to those of ordinary skill in the art (see *Antibodies: A Laboratory Manual,* Harlow and Lane (eds.), supra). Suitable techniques include peptide or protein affinity columns, HPLC or RP-HPLC, purification on protein A or protein G columns, or any combination of these techniques.

Therefore, the invention provides monoclonal and polyclonal antibodies, and fragments thereof specific for L-2 mutant polypeptides, as well as chimeric and humanized antibodies and fragments specific for such polypeptides. Such antibodies can be additionally modified with, for example, a label or a therapeutic agent for the diagnosis or treatment of HIV.

The antibodies raised against the above-described L-2 proteins can be used in quantitative, semi-qualitative, or qualitative diagnostic assays. Such assays, for example, can be in RIA, IRMA, and ELISA formats. Examples of such formats include a competitive or sandwich arrangement. See, for example, David et al., U.S. Pat. No. 4,486,530, issued Dec. 4, 1984; Motagnier et al., U.S. Pat. No. 4,708,818, issued Nov. 24, 1987; Montagnier et al., U.S. Pat. No. 5,135,864, issued Aug. 4, 1993; Gallo et al., U.S. Pat. No. 4,647,773, issued Mar. 3, 1987; Gallo et al., U.S. Pat. No. 4,520,113, issued May 28, 1985; and Gallo et al., U.S. Pat. No. 4,652,599, issued Mar. 24, 1987, all of which are herein incorporated by reference. In a competitive format, the instant antibodies are incubated with the sample to be analyzed and a measured quantity of labeled, competing analyte. The antibody in competitive assay is usually bound to a solid support, or is capable of being bound to such a support, as discussed below. Such binding to a solid support can take place before or after the instant antibody is incubated with the sample suspected of containing one of the instant proteins. In a sandwich format, two antibodies, each specific for the analyte, are reacted one at a time or simultaneously with the sample to be analyzed. Typically, one of the instant antibodies will be either be labeled with a detection means or capable of being so and the other will either be attached to a solid support or capable of being so. After the antibody-analyte-antibody sandwich complex is formed, the detection means is measured. Alternatively, after the complex is formed, the complex is then attached to a solid support or to a detection means, or both.

Binding to the solid support can be accomplished by an antibody that in turn binds to one of the antibodies of the complex, the natural or covalent attachment of the unlabeled antibody to the support, or by the reaction of another ligand-receptor pair, such as biotin-avidin. In the latter case, biotin is bound either to the constant region of the antibody or to the solid support and avidin is bound to the remaining component. In either the competitive or sandwich format, there are usually wash, aspiration and possibly filter procedures after the incubation of the sample and following the additions of each reagent.

The antibodies used in the above diagnostic assays can use, for example, one or more of the instant polyclonal or monoclonal antibodies, mixtures thereof, and the corresponding functional fragments. For example, in a sandwich assay, the two antibodies used to form the complex can either both be polyclonal or monoclonal or functional fragments thereof. Alternatively, one monoclonal and one polyclonal can form the sandwich. Similarly, in the competitive format, the antibody can be one or more monoclonal or polyclonal antibodies, or functional fragments thereof.

The detection means are well known in the art. Such detection means can be, for example, enzymes, radioisotopes, fluorogens, chromogens, metallic or non-metallic colloids, colored liposomes, colored or colorable particles, and the like. Thus, the detection means may be immediately visible after the analyte complexes with the instant antibodies in an assay, or further steps may need to be taken to utilize the detection means. Such steps include UV and visible spectrophotometry, fluorimetry and analysis by radiation counters. Examples of such detection means include alkaline phosphatase/para-nitrophenyl phosphate; horse radish peroxidase/aminoethylcarbazole, colloidal gold, colloidal silver, colloidal selenium, hydrophobic dyes, colored latex microparticles, carbon sols, rhodamine, fluorescein, luminol, luciferin, umbeliferone, $^{125}$Iodine, $^{131}$Iodine, tritium, $^{32}$Phosporous, and the like. These detection means can be coupled to the either the analyte (competitive assays) or to an antibody (sandwich assays) by means well known in the art. Suitable detection means and methods of making them are further discussed, for example, in Tom et al., U.S. Pat. No. 4,366,241, issued Dec. 28, 1982; and in Campbell, U.S. Pat. No. 4,703,017, issued Oct. 27, 1987.

The optional solid supports for the assays can be bibulous or nonbibulous. Examples of bibulous supports include nitrocellulose, nylon, filter paper, and the like. Non-bibulous supports are ones that do not necessarily effect a chromatographic separation of the components as they advance along the solid support. Examples of such non-bibulous supports include plastic materials such as high density polyethylene, polystyrene, polyvinyl chloride, mixtures of such high density plastics, or bibulous material rendered non-bibulous by the application of non-blocking materials, such as detergents and proteins. These and other supports and methods of use are known in the art.

The invention also provides diagnostic kits comprising the L-2 specific antibodies. In addition, such kits can contain amounts of reagents for use in assaying for an analyte. Such reagents can be substrates when enzymes are used as the detection means, as well as ancillary reagents like stabilizers, extraction reagents, buffers, wash solutions, and the like. The relative amounts of the various reagents vary widely, to provide for concentrations in solution of the reagents which substantially optimize the sensitivity of the assay. The reagents can be provided as dry powders, usually lyophilized, including excipients, which on dissolution will provide for a reagent solution having the appropriate concentrations for performing the assay. The kit can also be contained in packaging material, such as air-tight foil, or various external containers known in the art. Such external containers can contain the device, reagents, and the instructions for use of the assays.

It is understood that modifications which do not substantially affect the activity of the various embodiments of this invention are also included within the definition of the invention provided herein. Accordingly, the following examples are intended to illustrate but not limit the present invention.

EXAMPLE I

This Example describes the determination of the genetic makeup of the HIV-1 provirus in L-2 cells.

In initial studies the cleavage pattern of the HIV-1 Gag polypeptide expressed in *Escherichia coli* transformed with recombinant L-2 gag containing an HIV-1 wild-type pol protease gene was found to be similar to that of parental HIV-1 (LAI) particles. Therefore, the L-2 cell provirus was sequenced at other regions of the genome. Other regions of the L-2 cell proviruses genome that were sequenced included pol protease; env gp120 (SU) and gp41 (TM); and the accessory region genes such as vif, vpu, vpr, and nef. The control was the provirus in MOLT-4 cells (ATCC) persistently infected with HIV-1 (LAI), which was designated as MO/LAI was used as a control.

The polymerase chain reaction (PCR) amplification of total cellular DNA extracted from L-2 and MO/LAI was performed as previously described (Kameoka et al., *Virus Genes*, 12:117–129 (1996), utilizing 30 cycles of 1 min at 94° C., 4 min at 60° C., followed by a final polymerization step for 10 min at 72° C., with a GeneAmp XL PCR kit (Perkin-Elmer Corlporation, Foster City, Calif.). The primers used at each region are summarized in FIG. 2 (Adachi et al., *J. Virol*, 59:284–291 (1986). The PCR products were separated by agarose gel electrophoresis and visualized by ethidium bromide staining. The expected bands were ligated into a pBluescript II SK(−) vector (Stratagene Cloning Systems, La Jolla, Calif.). Nucleotide sequencing of the amplified DNA segments was carried out using ($\gamma$-$^{32}$P)ATP-labeled T3, T7, or synthetic primers by cycle sequencing according to the protocol described for the CircumVent thermal cycle sequencing kit (New England BioLabs, Beverly, Mass.).

The nucleotide sequences of provirus genes in the L-2 cells were compared with those determined from MO/LAI as well as the reported HIV-1 (LAI) sequences (GenBank accession number K02013)(Wain-Hobson et al., Cell, 40:9–17 (1985),(see FIG. 1). Comparison of the nucleotide sequences of provirus genes to the nucleotide sequences HIV-1, LAI and HIV-1 MO/LAI genes reveals significant mutations in the pol protease, env gp41, and nef genes for L-2 proviral DNA. Specifically, the protease gene had an insertion mutation of T at nucleotide position 42, resulting in the appearance of a stop codon at amino acid residue 30. This explains the protease-defective nature of L-2 particles, as evidenced by an inability to cleave the Pr55gag precursor inside L-2 cells. For the TM envelope glycoprotein, gp41, a 1-base substitution was found at nucleotide 7781 (A to G; corresponding to nucleotide 1979 in FIG. 1), resulting in an amino acid substitution at amino acid residue 660, from a lysine to an arginine. The nef gene also had a nonsense mutation at nucleotide 8559 (G to A; corresponding to nucleotide 170 in FIG. 1), resulting in the appearance of a stop codon at amino acid residue 57, as well as other mutations set forth in FIG. 3. All three of these changes in the protease, gp41, and nef genes were specific for L-2 proviral DNA.

In contrast, the vpr gene was similarly truncated for both L-2 and MO/LAI proviral DNAs owing to a 1-base substitution at nucleotide 5194 (G to A; corresponding to nucleotide 54 in FIG. 1), resulting in the appearance of a stop codon at amino acid residue 18. The vif and vpu genes were identical for both L-2 and MO/LAI proviral DNAs. Also, the sequencing of env gp120 revealed no apparent differences between L-2 and MO/LAI although both showed V1 and V2 domains that contained deletions of either eight or two amino acids, respectively, as compared to the reported HIV-1 (LAI) sequence. Therefore it is possible that these deletions in gp120 could have occurred during the long-term maintenance of HIV-1 (LAI) in different T cell lines during the instant studies, with no apparent effect on their infectivity.

The data presented here point to the specific involvement of one or more mutation(s) in the L-2 provirus pol protease, env gp41, and/or nef genes as the cause for the production of defective, but highly syncytium- and apoptosis-inducing particles. In particular, the amino acid mutation at Env gp41accounts for the higher functional activity of protease-defective particles. Furthermore, the gp120 polypeptide deletions of 8 and 2 amino acids corresponding to SEQ ID NOS:18 and 24 (FIG. 1), respectively, are critical in defining the pathogenicity of L-2 particles in the context of the L-2 Nef, protease, gp41, or Vpr mutant-derived polypeptides. These L-2 particles are responsible for causing the highly pathogenic end-stages of HIV-1 disease leading to ARC and AIDS. Thus, it is important to stimulate the immune system to attack any defective L-2 particles that accumulate during infection. The use of inactivated L-2 particles, optionally in conjunction with other HIV-1 or HIV-2 immunogens, or both, nucleic acid sequences and fragments, polypeptides and fragments thereof, and antibodies, as described in this invention, alone or in combination thereof, will remove potentially harmful defective L-2 particle from HIV-1 infected tissues of individuals, leading to an improved outcome.

These results show that HIV-1 provirus from L-2 cells have mutations in the pol protease, nef, env and vpr genes that encode the pol protease, Nef, gp41, gp120 and Vpr polypeptides and result in mutations in these polypeptides.

EXAMPLE II

Production of Non-infectious, L-2 Particles or Modified Forms Thereof

This Example describes the production of non-infectious L-2 particles or modified forms thereof. The method of production of non-infectious, L-2 particles or modified forms thereof has essentially been described previously with some modifications (Prior et al., (1995); Prior et al. (1996)). The modifications are related to the cell culture and downstream recovery conditions to improve both production levels and purification of virus from the growth medium containing 5–10% fetal bovine serum.

The production method for L-2 particles will mimic those used for HIV-1 described below. The initial production steps involve anion exchange chromatography. Briefly, the cell line used is the L-2 cell line. After multiple cell culture expansions with cell densities in the range of one to two million cells per milliliter, the cellular debris is separated from virus by dead-end filtration using a 1.2 $\mu$M cellulose ester membrane. The filtered supernatant containing L-2 particles is inactivated by addition of β-propiolactone (1:2000 v/v), concentrated by tangential flow ultrafiltration using a 300,000 molecular weight (MW) cut-off polysulphone membrane and the concentrates are stored at −70° C. This hold step permits analysis of in-process material in an infectivity assay to determine that infectious virus is non-detectable before further processing. Thawed concentrates are pooled, filtered and applied to TMAE Fractogel (Merck, Darmstadt, Germany), washed with 0.5M NaCl at pH 6.5 and eluted in 1.0M Ncl at pH 6.5. After immediate dilution to reduce NaCl concentration to about 0.15M, product is applied to Q-Sepharose (Pharmacia, Inc., Piscataway, N.J., USA), washed in 0.7M NaCl and eluted in 1.0M NaCl, all at pH 6.5. Following concentration/diafiltration (polysulphone, 3000 MW cut-off), product is centrifuged and the pellet is resuspended, then frozen and subjected to γ irradiation on dry ice. The combined inactivation steps, β-propiolactone and γ irradiation, can be validated to attain a >17 log viral inactivation capability.

Briefly, the pooled filtrate containing product is inactivated with β-propiolactone (βPL) and subjected to ultrafiltration. Briefly, following pH adjustment of the pooled filtrate to 7.3±0.1, βPL is added while stirring to a final concentration of 1:2,000 (v/v). After stirring for one hour, the preparation is transferred to a second mixing vessel to ensure complete viral inactivation and incubated at 4° C. for 18–24 hours with continuous stirring. The temperature of the filtrate is raised to 37° C. and maintained at that temperature for approximately five hours to hydrolyze residual βPL into an isomer of lactate and betapropionic acid derivatives. Approximately 10–200 liters of post βPL-treated filtrate is concentrated to 2.5–3.5 liters using a polysulfone 300,000 molecular weight (MW) cutoff membrane and diafiltered against 10–20 volumes of phosphate buffered saline. This step removes more than 95% of the growth medium-derived polypeptide from the permeate, including approximately 50% of the starting p24 antigen as measured by ELISA. In this MW fraction (less than 300 kDa), p24 antigen is not associated with intact particles. The MW cutoff properties of the membrane achieves almost total retention of intact particles. The concentrate is stored frozen at −70° C. This is a critical hold step because individual concentrates, derived from a single expansion of cell culture, can be thawed and pooled to the required lot size for subsequent chromatography. This hold step can be used for quality control to determine which concentrates to release for further processing, after conducting sterility testing and after verifying that a cell culture is free of adventitious virus and mycoplasma. This in-process check before pooling can prevent compromising large lot sizes, thus avoiding economic risk while maintaining the safety and integrity of a process.

Validating the use of βPL for inactivating HIV-1 is another critical safety measure. To determine the effectiveness of inactivating HIV-1 with βPL, a high concentrate of infectious virus is used at 0 time (starting time, pre-βPL). βPL is added (1:2,000 v/v), and the decay in infectivity and βPL is evaluated. After adding βPL, samples are taken hourly, βPL activity is immediately neutralized with sodium sulfite, and the material is maintained at −70° C. pending analysis of the infectivity and βPL assays. Evaluation of inactivation is computed by subtracting the final log concentration at the time point measured from the log concentration of infectious HIV-1 at 0 time (pre-βPL). Previous unpublished work has shown that, within 12 hours, infectious virus is either nondetectable or at trace levels, and absolute inactivation is confirmed 18 hours after βPL is added. Because the half-life of βPL in production medium is approximately 19 hours, sufficient residual βPL exists to continue inactivation beyond the 12–18 hours during which infectious virus is nondetectable. Therefore, to evaluate the inactivation potential for the entire production time of $\leq 53$ hours, a fresh concentration of infectious HIV-1 is added in the form of an infectious spike to the βPL-treated material after 12 hours to determine the cumulative inactivation. Separate validation runs can performed in duplicate.

For large scale cell culture and harvest of L-2 particles, the cell line used is L-2 cells. Briefly, frozen vials of L-2 cells are thawed and cultures are initiated. The culture medium throughout most of the expansion process is 10% fetal bovine serum (FBS) in RPM1-1640 with 25 mM HEPES-N-(2-hydroxyethyl)piperazine-N'-2-ethanesulphonic acid. As the cells divide, the culture volume is expanded to larger vessels and sparged daily with 5% $CO_2$/air. In the final expansion (from approximately 72L to a final volume of 144 L), the FBS content is reduced to about 7.5% with 5.0% FBS in RPM1-1640 and 25 nM HEPES. Virus is separated from intact cells and cellular debris using a 1.2-μm cellulose ester filter. The pooled filtrate-containing product is cooled and maintained at 4° C. The entire cell culture production cycle, from the initial thaw of cells to the harvest of the final expansion takes approximately 35–45 days.

For cobalt irradiation and final formulation, the frozen, postchromatography product is removed from a biosafety level 3 (BSL-3) containment facility and on dry ice is subjected to 4.5–5.5 Mrad of cobalt irradiation. The objective is to optimize virus inactivation potential and minimize alteration to polypeptide structure to produce an immunogen. Cobalt irradiation inactivates virus by shearing nucleic acid into pieces of approximately 200 base pairs (bp), as determined by polymerase chain reaction (PCR), rendering virus biologically dysfunctional. The HIV-1 inactivation efficiency of cobalt irradiation is evaluated by aliquoting a given preparation of starting high-tier infectious virus and subjecting each sample maintained at −70° C. to a single dose level of irradiation. Individual alquots are subjected to 1.0, 2.0, 3.0, 4.0, 5.0 Mrad and measured for levels of infectivity. The study is performed in triplicate using three separate lots of infectious virus. The log reduction of infectivity is determined in primary peripheral blood mononuclear cells using the starting infectious titer following 5 Mrads of irradiation. The mean reduction in infectivity is expected to be 7 logs.

Cobalt irradiation also functions to sterilize the product. This is important because, unlike polypeptide solutions, purified HIV-1 particles such as non-infectious, L-2 particles or modified forms thereof cannot be subjected to sterile filtration techniques. A 0.2 μm filter retains HIV-1 particles. Following irradiation, product is thawed, diluted with saline to a required dose, and emulsified with an equal volume of incomplete Freund's adjuvant. Syringes are filled for intramuscular administration with final bulk product—an off-white, viscous emulsion. Consistent sterility of product is maintained by performing formulation steps in an aseptic area supplied with high quality air such as class 100 filtered air maintained under positive pressure.

Inactivated purified product is thawed, polypeptide content determined, diluted in saline and emulsified with an equal volume of incomplete Freund's adjuvant (IFA) (Seppic Inc. Paris, France), to achieve a water:oil ratio of 1:1. All liquids and containers are maintained at 2–8° C. to attain an optimal viscosity. The bulk product is filled into syringes for intramuscular administration.

To determine the purity of the final viral particle product, analytical gel-filtration chromatography is used. Analytical gel-filtration chromatography CL6B resin (Pharmacia Inc.) is packed into a 16 mm×310 mm low-pressure Pharmacia XK16 column. The total column volume is about 60 ml. Low-pressure chromatography conditions are employed during the separation procedure to ensure that the virion remains intact, including use of a non-denaturing buffer system. The running buffer is 0.1M Tris and 0.5M NaCl, pH 8.0. This ionic strength eliminates any adsorption of the virion onto the resin. The CL6B resin is highly crosslinked and has a MW fractionation range between 10 and 4000 kDa (molecules with a MW>4000 kDa are eluted in the void volume). The column is controlled by a Perspective Biosystems BioCAD 60 control system (Cambridge, Mass. USA) at a flow rate of 2 ml min. Chromatographic profiles are monitored at two wavelengths: 230 and 280 nm. To determine HIV-1 antigen recovery and calculate mass balance, approximately 1.5 ml fractions are collected.

The non-infectious, L-2 particles or modified forms thereof produced by the procedure described above can be used for the prevention or treatment of diseases caused by HIV infection.

Throughout this application various publications have been referenced within parentheses. The disclosures of these publications in their entireties are hereby incorporated by reference in this application in order to more fully describe the state of the art to which this invention pertains.

Although the invention has been described with reference to the disclosed embodiments, those skilled in the art will readily appreciate that the specific experiments detailed are only illustrative of the invention. It should be understood that various modifications can be made without departing from the spirit of the invention. Accordingly, the invention is limited only by the following claims.

What is claimed is:

1. An immunogen comprising an inactivated protease-defective viral HIV-1 particle containing one or more of the following proteins:

an HIV-l Env gp120 protein comprising substantially the same amino acid sequence of a mutated HIV-1 Env qp120 protein or fragment thereof selected from the group consisting of:

(a) the amino acid sequence of an HIV-1 Env qp120, wherein amino acid residue 143 is either serine or arginine; up to eight amino acids at amino acid residues 144 through 151 in the V1 domain are deleted; and amino acid residue 153 is either methionine or isoleucine, as in SEQ ID NO:18; and (b) the amino acid sequence of an HIV-1 Env gp120, wherein amino acid residue 187 is either isoleucine or valine; and one or two amino acids at amino acid residues 192 and 193 in the V2 domain are deleted, as in SEQ ID NO:24;

a mutated HIV-1 Pol protease molecule comprising substantially the same sequence of amino acid residues 1 through 13 of a wild-type HIV-1 Pol protease protein and amino acid residues 14 through 29 of SEQ ID NO:6;

a truncated HIV-1 Nef protein or fragment thereof comprising substantially the same sequence of amino acid residues 1 through 56 of an HIV-1 Nef protein of SEQ ID NO:46;

a mutated HIV-1 Nef protein comprising substantially the same amino acid sequence set forth in SEQ ID NO:46 or a fragment thereof comprising one or more of the following amino acid residues of SEQ ID NO:46: alanine at amino acid residue 15, lysine at amino acid residue 19, valine at amino acid residue 33, and aspartic acid at amino acid residue 54;

a truncated HIV-1 Nef protein comprising substantially the same sequence of amino acid residues 1 through 56 of a Nef peptide of SEQ ID NO:46, wherein amino acid residue 54 is aspartic acid;

a truncated HIV-1 Vpr protein or fragment thereof comprising substantially the same amino acid residues 1 through 17 of an HIV-1 Vpr protein of SEQ ID NO:12; or an HIV-1 Env gp41 protein or fragment thereof comprising substantially the same amino acid sequence of an HIV-1 Env gp41 protein containing an arginine at amino acid residue 660, as in SEQ ID NO:30.

2. The immunogen of claim 1 further comprising one or more suitable adjuvants.

3. The immunogen of claim 1, comprising an HIV-1 Env gp120 protein comprising substantially the same amino acid sequence as a mutated HIV-1 Env gp120 protein or a fragment thereof, wherein amino acid residue 143 is either serine or arginine; up to eight amino acids within amino acid residues 144 through 151 are deleted; and amino acid residue 153 is either methionine or isoleucine, as in SEQ ID NO:18.

4. The immunogen of claim 1, comprising an HIV-1 Env gp120 protein comprising substantially the same amino acid sequence as a mutated HIV-1 Env gp120 protein or a fragment thereof, wherein amino acid residue 187 is either isoleucine or valine; and one or both of amino acid residues 192 and 193 are deleted, as in SEQ ID NO:24.

5. The immunogen of claim 1, comprising a mutated HIV-1 Pol protease molecule comprising substantially the same sequence of amino acid residues 1 through 13 of a wild-type HIV-1 Pol protease protein and amino acid residues 14 though 29 of SEQ ID NO:6.

6. The immunogen of claim 1, comprising a truncated HIV-1 Nef protein or fragment thereof, comprising substantially the same sequence of amino acid residues 1 through 56 of an HIV-1 Nef protein of SEQ ID NO:46.

7. The immunogen of claim 1, comprising a substantially pure mutated HIV-1 Nef protein comprising substantially the same amino acid sequence set forth in SEQ ID NO:46 or a fragment thereof, comprising one or more of the following amino acid residues of SEQ ID NO:46: alanine at amino acid residue 15, lysine at amino acid residue 19, valine at amino acid residue 33, and aspartic acid at amino acid residue 54.

8. The immunogen of claim 1, comprising a truncated HIV-1 Nef protein comprising substantially the same sequence of amino acid residues 1 through 56 of a Nef peptide of SEQ ID NO:46, wherein amino acid residue 54 is aspartic acid.

9. The immunogen of claim 1, comprising a truncated HIV-1 Vpr protein or fragment thereof comprising substantially the same amino acid residues 1 through 17 of an HIV-1 Vpr protein of SEQ ID NO:12.

10. The immunogen of claim 1, comprising an HIV-1 Env gp41protein or fragment thereof, comprising substantially the same amino acid sequence of an HIV-1 Env gp41protein, wherein amino acid residue 660 is arginine, as in SEQ ID NO:30.

11. The immunogen of claim 1, comprising an HIV-1 Env gp120 protein comprising a mutated HIV-1 Env gp120 protein or a fragment thereof, wherein amino acid residue 143 is either serine or arginine; up to eight amino acids within amino acid residues 144 through 151 are deleted; and amino acid residue 153 is either methionine or isoleucine, as in SEQ ID NO:18.

12. The immunogen of claim 1, comprising an HIV-1 Env gp1120 protein comprising a mutated HIV-1 Env gp120 protein or a fragment thereof, wherein amino acid residue 187 is either isoleucine or valine; and one or both of amino acid residues 192 and 193 are deleted, as in SEQ ID NO:24.

13. The immunogen of claim 1, comprising a mutated HIV-1 Pol protease molecule comprising amino acid residues 1 through 13 of a wild-type HIV-1 Pol protease protein and amino acid residues 14 through 29 of SEQ ID NO:6.

14. The immunogen of claim 1, comprising a truncated HIV-1 Nef protein or fragment thereof, comprising amino acid residues 1 through 56 of an HIV-1 Nef protein of SEQ ID NO:46.

15. The immunogen of claim 1, comprising a mutated HIV-1 Nef protein comprising the amino acid sequence set forth in SEQ ID NO:46 or a fragment thereof, comprising one or more of the following amino acid residues of SEQ ID NO:46: alanine at amino acid residue 15, lysine at amino acid residue 19, valine at amino acid residue 33, and aspartic acid at amino acid residue 54.

16. The immunogen of claim 1, comprising a truncated HIV-1 Nef protein comprising amino acid residues 1 through 56 of a Nef peptide of SEQ ID NO:46, wherein amino acid residue 54 is aspartic acid.

17. The immunogen of claim 1, comprising a truncated HIV-1 Vpr protein or fragment thereof comprising amino acid residues 1 through 17 of an HIV-1 Vpr protein of SEQ ID NO:12.

18. The immunogen of claim 1, comprising an HIV-1 Env gp41protein or fragment thereof, having the amino acid sequence of HIV-1 Env gp41, wherein amino acid residue 660 is arginine, as in SEQ ID NO:30.

19. An immunogen comprising an inactivated protease-defective viral HIV-1 particle containing one or more of the following proteins:

an HIV-1 Env gp120 protein comprising substantially the same amino acid sequence of a HIV-1 Env gp120 protein or fragment thereof selected from the group consisting of:

(a) the amino acid sequence of an HIV-1 Env gp120, wherein amino acid residue 143 is either serine or arginine; up to eight amino acids at amino acid residues 144 through 151 in the V1 domain are deleted; and amino acid residue 153 is either methionine or isoleucine, as in SEQ ID NO:18; and (b) the amino acid sequence of an HIV-1 Env gp120, wherein amino acid residue 187 is either isoleucine or valine; and one or two amino acids at amino acid residues 192 and 193 in the V2 domain are deleted, as in SEQ ID NO:24;

a mutated HIV-1 Pol protease molecule comprising substantially the same sequence of amino acid residues 1 through 13 of a wild-type HIV-1 Pol protease protein and amino acid residues 14 through 29 of SEQ ID NO:6;

a truncated HIV-1 Nef protein or fragment thereof comprising substantially the same sequence of amino acid residues 1 through 56 of an HIV-1 Nef protein of SEQ ID NO:48;

a mutated HIV-1 Nef protein comprising substantially the same amino acid sequence set forth in SEQ ID NO:46 or a fragment thereof comprising one or more of the following amino acid residues of SEQ ID NO:48: alanine at amino acid residue 15, lysine at amino acid residue 19, valine at amino acid residue 33, and aspartic acid at amino acid residue 54;

a truncated HIV-1 Nef protein comprising substantially the same sequence of amino acid residues 1 through 56 of a Nef peptide of SEQ ID NO:48, wherein amino acid residue 54 is aspartic acid;

a truncated HIV-1 Vpr protein or fragment thereof comprising substantially the same amino acid residues 1 through 17 of an HIV-1 Vpr protein of SEQ ID NO:12; or an HIV-1 Env gp41protein or fragment thereof comprising substantially the same amino acid sequence of an HIV-1 Env gp41protein containing an arginine at amino acid residue 660, as in SEQ ID NO:30.

20. The immunogen of claim 19, comprising a truncated HIV-1 Nef protein or fragment thereof, comprising amino acid residues 1 through 56 of an HIV-1 Nef protein of SEQ ID NO:48.

21. The immunogen of claim 19, comprising a mutated HIV-1 Nef protein comprising the amino acid sequence set forth in SEQ ID NO:48 or a fragment thereof, comprising one or more of the following amino acid residues of SEQ ID NO:48: alanine at amino acid residue 15, lysine at amino acid residue 19, valine at amino acid residue 33, and aspartic acid at amino acid residue 54.

22. The immunogen of claim 19, comprising a truncated HIV-1 Nef protein comprising amino acid residues 1 through 56 of a Nef peptide of SEQ ID NO:48, wherein amino acid residue 54 is aspartic acid.

* * * * *

UNITED STATES PATENT AND TRADEMARK OFFICE
CERTIFICATE OF CORRECTION

PATENT NO. : 6,328,976 B1
DATED : December 11, 2001
INVENTOR(S) : Luftig

It is certified that error appears in the above-identified patent and that said Letters Patent is hereby corrected as shown below:

Column 39,
Lines 47 and 49, please delete "qp120" and replace with -- gp120 --.

Signed and Sealed this

Sixteenth Day of September, 2003

JAMES E. ROGAN
*Director of the United States Patent and Trademark Office*